(12) United States Patent
Hedrick et al.

(10) Patent No.: US 10,953,039 B2
(45) Date of Patent: *Mar. 23, 2021

(54) UTILIZING POLYMERS AND ANTIBIOTICS TO ENHANCE ANTIMICROBIAL ACTIVITY AND INHIBIT ANTIBIOTIC RESISTANCE

(71) Applicants: International Business Machines Corporation, Armonk, NY (US); Agency for Science, Technology and Research, Singapore (SG)

(72) Inventors: James L. Hedrick, Pleasanton, CA (US); Simone Bianco, San Francisco, CA (US); Mark Kunitomi, San Francisco, CA (US); Yi Yan Yang, Singapore (SG); Xin Ding, Singapore (SG); Chuan Yang, Singapore (SG); Zhen Chang Liang, Singapore (SG); Paola Florez de Sessions, Singapore (SG); Balamurugan Periaswamy, Singapore (SG)

(73) Assignees: INTERNATIONAL BUSINESS MACHINES CORPORATION, Armonk, NY (US); AGENCY FOR SCIENCE, TECHNOLOGY AND RESEARCH, Connexis (SG)

( * ) Notice: Subject to any disclaimer, the term of this patent is extended or adjusted under 35 U.S.C. 154(b) by 0 days.

This patent is subject to a terminal disclaimer.

(21) Appl. No.: 16/144,040

(22) Filed: Sep. 27, 2018

(65) Prior Publication Data

US 2020/0101105 A1 Apr. 2, 2020

(51) Int. Cl.
| | |
|---|---|
| A61K 31/785 | (2006.01) |
| A61P 31/04 | (2006.01) |
| A61K 31/407 | (2006.01) |
| A61K 31/496 | (2006.01) |
| A61K 31/7052 | (2006.01) |
| A61K 31/43 | (2006.01) |

(52) U.S. Cl.
CPC ............ *A61K 31/785* (2013.01); *A61P 31/04* (2018.01); *A61K 31/407* (2013.01); *A61K 31/43* (2013.01); *A61K 31/496* (2013.01); *A61K 31/7052* (2013.01); *A61K 2300/00* (2013.01)

(58) Field of Classification Search
None
See application file for complete search history.

(56) References Cited

U.S. PATENT DOCUMENTS

| | | |
|---|---|---|
| 6,464,971 B1 | 10/2002 | Matthews et al. |
| 7,169,814 B2 | 1/2007 | Rothbard et al. |
| 7,862,807 B2 | 1/2011 | Goodman et al. |
| 7,939,621 B2 | 5/2011 | Cooley et al. |
| 8,449,916 B1 | 5/2013 | Bellaire et al. |
| 8,586,705 B2 | 11/2013 | Krippner et al. |
| 9,854,806 B2 | 1/2018 | Chin et al. |
| 2005/0249818 A1 | 11/2005 | Sawan et al. |
| 2013/0274173 A1 | 10/2013 | Cheng et al. |
| 2016/0338356 A1* | 11/2016 | Chin ............... A01N 47/44 |

FOREIGN PATENT DOCUMENTS

| | | |
|---|---|---|
| CN | 1861663 A | 11/2006 |
| CN | 101747363 A | 6/2010 |
| CN | 103980385 A | 8/2014 |
| EP | 2 338 923 A1 | 6/2011 |
| WO | 01/79359 A2 | 10/2001 |
| WO | 2013/036352 A2 | 3/2013 |
| WO | 2014/168762 A1 | 10/2014 |
| WO | 2014/168771 A2 | 10/2014 |

OTHER PUBLICATIONS

Cho et al. "Molecular Weight and Charge Density Effects of Guanidinylated Biodegradable Polycarbonates on Antimicrobial Activity and Selectivity", BioMacromolecules, 19, 2018, pp. 1389-1401. (Year: 2018).*
Chin, Willy, et al. "A macromolecular approach to eradicate multidrug resistant bacterial infections while mitigating drug resistance onset." Nature Communications, (2018) 9:917. 14 pages.
Li, Qiaoying, et al. "Construction of Supramolecular Nanoassembly for Responsive Bacterial Elimination and Effective Bacterial Detection." Applied Materials & Interfaces, 2017, 9, 10180-10189. 10 pages.
Ng, Victor Wee Lin, et al. "Synergistic Co-Delivery of Membrane-Disrupting Polymers with Commercial Antibiotics against Highly Opportunistic Bacteria." Advanced Materials, Sep. 9, 2013. 7 pages.
Ng, Victor W.L., et al. "Antimicrobial hydrogels: A new weapon in the arsenal against multidrug-resistant infections." Advanced Drug Delivery Reviews, 78 (2014) 46-62. 17 pages.
Uppu, Divakara S. S. M., et al. "Membrane-Active Macromolecules Resensitize NDM-1 Gram-Negative Clinical Isolates to Tetracycline Antibiotics." PLOS ONE, Mar. 19, 2015. 15 pages.
Wang, "Biodegradable functional polycarbonate micelles for controlled release of amphotericin B." Acta Biomaterialia 46 (2016) 211-220. 10 pages.
Cooley, et al., "Oligocarbonate Molecular Transporters: Oligomerization-Based Syntheses and Cell-Penetrating Studies", J. AM. CHEM. SOC. 2009, 131, 16401-16403; Published on Web Oct. 27, 2009.
Edward, et al., "Organocatalytic Synthesis of Quinine-Functionalized Poly(carbonate)s", Biomacromolecules 2012, 13, 2483-2489; Published: Jul. 31, 2012.

(Continued)

*Primary Examiner* — Melissa L Fisher
(74) *Attorney, Agent, or Firm* — Amin, Turocy & Watson, LLP

(57) ABSTRACT

Techniques regarding treating one or more microbe infections with combination therapy are provided. For example, one or more embodiments described herein can comprise a method, which can comprise enhancing an antimicrobial activity of an antibiotic by a combination therapy. The combination therapy can comprise the antibiotic and a polycarbonate polymer functionalized with a guanidinium functional group.

8 Claims, 20 Drawing Sheets

(56) References Cited

OTHER PUBLICATIONS

Gabriel, et al., "Synthetic Mimic of Antimicrobial Peptide with Nonmembrane-Disrupting Antibacterial Properties", Biomacromolecules 2008, 9, 2980-2983; Published on Web Oct. 14, 2008.
Geihe, et al.,"orgDesigned guanidinium-rich amphipathic oligocarbonate molecular transporters complex, deliver and release siRNA in cells", Proceedings of the National Academy of Sciences of the United States of America,vol. 109, No. 33 (Aug. 14, 2012), pp. 13171-13176.
Locock, et al., "Guanylated Polymethacrylates: A Class of Potent Antimicrobial Polymers with Low Hemolytic Activity", Biomacromolecules 2013, 14, 4021-4031; Published: Oct. 7, 2013.
Pratt, et al., "Exploration, Optimization, and Application of Supramolecular Thiourea-Amine Catalysts for the Synthesis of Lactide (Co)polymers", Macromolecules 2006, 39, 7863-7871;Published on Web Oct. 18, 2006.
Pratt et al., "Tagging alcohols with cyclic carbonate: a versatile equivalent of (meth)acrylate for ring-opening polymerization", Chem. Commun., 2008, 114-116.
Zhou, et al., "Synthesis and Characterization of Novel Aliphatic Poly(carbonate-ester)s with Functional Pendent Groups", Macromol. Rapid Commun. 2005, 26, 1309-1314.
Non-Final Office Action received for U.S. Appl. No. 14/715,690 dated Aug. 12, 2016, 60 pages.
Non-Final Office Action received for U.S. Appl. No. 14/715,690 dated Jan. 9, 2017, 10 pages.
Final Office Action received for U.S. Appl. No. 16/686,109 dated Sep. 4, 2020, 35 pages.
Timin et al. (Colloid Polym Sci, 293, 1667-1674, 2015) Synthesis and application of silica hybrids grafted with new guanidine-containing polymers as highly effective adsorbents for bilirubin removal.
Non-Final Office Action received for U.S. Appl. No. 16/686,109 dated Apr. 6, 2020, 34 pages.
Non-Final Office Action received for U.S. Appl. No. 15/645,838 dated Nov. 1, 2019, 27 pages.
Final Office Action received for U.S. Appl. No. 15/645,838 dated Mar. 20, 2020, 21 pages.
First Search report received for Chinese Patent Application Serial No. 201680026719.X dated Oct. 25, 2018, 02 pages.
First office Action received for Chinese Patent Application Serial No. 201680026719.X dated Nov. 5, 2018, 20 pages (Including English Translation).
Extended European Search Report received for European Patent Application Serial No. 16796851.0 dated Jan. 1, 2019, 09 pages.
Frere A. et al.,"Impact of the Structure of Biocompatible Aliphatic Polycarbonates on siRNA Transfection Ability", Biomacromolecules, vol. 16, No. 3, Jan. 20, 2015, 53 pages.
Siedenbiedel et aL,"Antimicrobial Polymers in Solution and on Surfaces: Overview and Functional Principles", Polymers, vol. 4, No. 1, Jan. 9, 2012, pp. 46-71.
Ono R. J. et al., "Biodegradable Block Copolyelectrolyte Hydrogels for Tunable Release of Therapeutics and Topical Antimicrobial SkinTreatment", ACS MACRO Letters, vol. 4, No. 9, Aug. 10, 2015, pp. 886-891.
International Search Report and Written Opinion received for PCT Application Serial No. PCT/SG2016/050234 dated Jul. 11, 2016, 13 pages.
List of IBM Patents or Applications Treated as Related.

* cited by examiner

| Bacteria | Antibiotic | MIC of antibiotics at different polymer concentration (μg/mL) | | | | |
|---|---|---|---|---|---|---|
| | 306 | w/o polymer | 1/16 x MIC$_p$* | 1/8 x MIC$_p$* | 1/4 x MIC$_p$* | 1/2 x MIC$_p$* |
| A. baumannii (ATCC 1789) | Azithromycin | 2 | 1 | 1 | 0.5 | 0.25 |
| | Ceftazidime | 7.8 | 7.8 | 7.8 | 7.8 | 3.9 |
| | Ciprofloxacin | 0.25 | 0.25 | 0.25 | 0.25 | 0.25 |
| | Gentamicin | 0.25 | 0.25 | 0.25 | 0.25 | 0.13 |
| | Imipenem | 0.5 | 0.5 | 0.5 | 0.5 | 0.13 |
| | Penicillin G | 62.5 | 62.5 | 62.5 | 62.5 | 7.8 |
| | Rifampicin | 3.9 | 2 | 2 | 0.13 | 0.002 |
| | Tetracycline | 2 | 2 | 2 | 2 | 1 |
| E. coli (ATCC 25922) | Azithromycin | 3.9 | 3.9 | 3.9 | 2 | 1 |
| | Ceftazidime | 0.5 | 0.5 | 0.5 | 0.5 | 0.25 |
| | Ciprofloxacin | 0.002 | 0.002 | 0.002 | 0.002 | 0.001 |
| | Gentamicin | 0.5 | 1.0 | 0.5 | 0.5 | 0.5 |
| | Imipenem | 0.25 | 0.25 | 0.25 | 0.25 | 0.25 |
| | Penicillin G | 125 | 125 | 125 | 125 | 62.5 |
| | Rifampicin | 7.8 | 7.8 | 3.9 | 0.5 | 0.016 |
| | Tetracycline | 0.25 | 0.25 | 0.25 | 0.25 | 0.25 |
| P. aeruginosa (ATCC 9027) | Azithromycin | 62.5 | 62.5 | 125 | 125 | 62.5 |
| | Ceftazidime | 3.9 | 3.9 | 3.9 | 3.9 | 2 |
| | Ciprofloxacin | 0.06 | 0.06 | 0.06 | 0.06 | 0.03 |
| | Gentamicin | 2 | 2 | 3.9 | 3.9 | 2 |
| | Imipenem | 3.9 | 3.9 | 3.9 | 7.8 | 3.9 |
| | Penicillin G | >500 | >500 | >500 | >500 | >500 |
| | Rifampicin | 16 | 16 | 16 | 16 | 7.8 |
| | Tetracycline | 15.6 | 15.6 | 15.6 | 7.8 | 2 |
| S. aureus (ATCC 6538) | Azithromycin | 0.25 | 0.25 | 0.25 | 0.25 | 0.25 |
| | Ceftazidime | 3.9 | 3.9 | 3.9 | 3.9 | 3.9 |
| | Ciprofloxacin | 0.125 | 0.125 | 0.125 | 0.125 | 0.125 |
| | Gentamicin | 0.25 | 0.25 | 0.25 | 0.25 | 0.125 |
| | Imipenem | <0.03 | <0.03 | <0.03 | <0.03 | <0.03 |
| | Penicillin G | 0.06 | 0.03 | 0.03 | 0.03 | 0.03 |
| | Rifampicin | <0.03 | <0.03 | <0.03 | <0.03 | <0.03 |
| | Tetracycline | <0.03 | <0.03 | <0.03 | <0.03 | <0.03 |

* MIC of antimicrobial polymer (MIC$_p$) against different bacteria: 15.6 μg/mL for A. baumannii, E. coli and P. aeruginosa, and 7.8 μg/mL for S. aureus

| Bacteria | Strain Number | MIC of Rifampicin at different polymer concentration (ppm) | | | |
|---|---|---|---|---|---|
| | | No polymer | 1/8 × $MIC_p$ | 1/4 × $MIC_p$ | 1/2 × $MIC_p$ |
| A. baumannii | ATCC 1709 | 3.9 | 2 | 0.13 | 0.002 |
| | ATCC 1789* | 2 | 2 | 0.5 | 0.004 |
| | ATCC 1792* | 3.9 | 2 | 0.5 | 0.004 |

| Bacteria | Strain Number | MIC of Imipenem at different polymer concentration (µg/mL) | | | |
|---|---|---|---|---|---|
| | | No polymer | 1/8 × $MIC_p$ | 1/4 × $MIC_p$ | 1/2 × $MIC_p$ |
| A. baumannii | ATCC 1709 | 0.5 | 0.5 | 0.5 | 0.125 |
| | ATCC 1789* | 15.6 | 7.8 | 3.9 | 0.25 |
| | ATCC 1792* | 62.5 | 62.5 | 31.3 | 3.9 |

| Bacteria | Strain Number | MIC of Azithromycin at different polymer concentration (µg/mL) | | | |
|---|---|---|---|---|---|
| | | No polymer | 1/8 × $MIC_p$ | 1/4 × $MIC_p$ | 1/2 × $MIC_p$ |
| A. baumannii | ATCC 1709 | 2 | 1 | 0.5 | 0.25 |
| | ATCC 1789* | 62.5 | 62.5 | 31.3 | 0.5 |
| | ATCC 1792* | 2000 | 1000 | 500 | 62.5 |

| Bacteria | Strain Number | MIC of Penicillin G at different polymer concentration (µg/mL) | | | |
|---|---|---|---|---|---|
| | | No polymer | 1/8 × $MIC_p$ | 1/4 × $MIC_p$ | 1/2 × $MIC_p$ |
| A. baumannii | ATCC 1709 | 62.5 | 62.5 | 62.5 | 7.8 |
| | ATCC 1789* | >2000 | >2000 | >2000 | 250 |
| | ATCC 1792* | >2000 | >2000 | >2000 | >2000 |

| Bacteria | MIC of colistin in the presence of Example Polycarbonate 200 at different concentration (μg/mL) | | | |
|---|---|---|---|---|
| | No polymer | 1/8 x $MIC_p$ | 1/4 x $MIC_p$ | 1/2 x $MIC_p$ |
| E. coli | 2 | 1 | 1 | 0.25 |
| K. pneumoniae | 2 | 2 | 0.5 | 0.06 |
| A. baumannii | 1 | 0.5 | 0.25 | 0.03 |

| Bacteria | MIC of polymer at different colistin concentration (μg/mL) | | | |
|---|---|---|---|---|
| | No colistin | 1/8 x $MIC_c$ | 1/4 x $MIC_c$ | 1/2 x $MIC_c$ |
| E. coli | 15.6 | 7.8 | 7.8 | 2 |
| K. pneumoniae | 31.3 | 15.6 | 7.8 | 7.8 |
| A. baumannii | 15.6 | 7.8 | 3.9 | 1 |

1200

| Antibiotic 306 | Bacterial Strain | MIC of antibiotics in the presence of Example Polycarbonate 200 at different concentrations (μg/mL) | | | |
|---|---|---|---|---|---|
| | | w/o adjuvant | 1/8 × MIC* | 1/4 × MIC* | 1/2 × MIC* |
| Rifampicin | A. B. BAA-1789* | 2.0 | 2.0 | 1.0 | 0.004 |
| | A. B. BAA-1792* | 3.9 | 2.0 | 1.0 | 0.004 |
| | K. P. 700603 | 31.3 | 15.6 | 2.0 | 0.13 |
| Azithromycin | A. B. BAA-1789* | 62.5 | 62.5 | 31.3 | 0.5 |
| | A. B. BAA-1792* | 2000 | 1000 | 500 | 62.5 |
| | K. P. 700603 | | | | |
| Imipenem | A. B. BAA-1789* | 15.6 | 7.8 | 3.9 | 0.25 |
| | A. B. BAA-1792* | 62.5 | 62.5 | 31.3 | 3.9 |
| | K. P. 700603 | | | | |

*MIC of Example Polycarbonate is 15.6 μg/mL for both strains of A.B. and 31.3 μg/mL for K. Pneumoniae

| Antibiotic 306 | Bacterial Strain | MIC of Rifampicin at different concentrations of Example Polycarbonate 200 (µg/mL) | | | |
|---|---|---|---|---|---|
| | | w/o adjuvant | 1/8 × MIC* | 1/4 × MIC* | 1/2 × MIC* |
| Rifampicin | A. baumannii 19606 | 2.0 | 1.0 | 0.5 | 0.004 |
| | E. aerogenes 13048 | 31.3 | 3.9 | 0.25 | 0.13 |
| | E. coli 25922 | 7.8 | 3.9 | 1.0 | 0.06 |

*MIC of Example Polycarbonate 200 is 15.6 µg/mL

1302

| Bacteria | Fold reduction of rifampicin MIC in presence of Example Polycarbonate 200 (7.8 µg/mL) |
|---|---|
| A. baumannii BAA-1789* | 512 |
| A. baumannii BAA-1792* | 1024 |
| K. pneumoniae * | 256 |
| A. baumannii BAA-1709 | 2048 |
| A. baumannii 19606 | 512 |
| E. aerogenes 13048 | 256 |
| E. coli 25922 | 128 |

1304

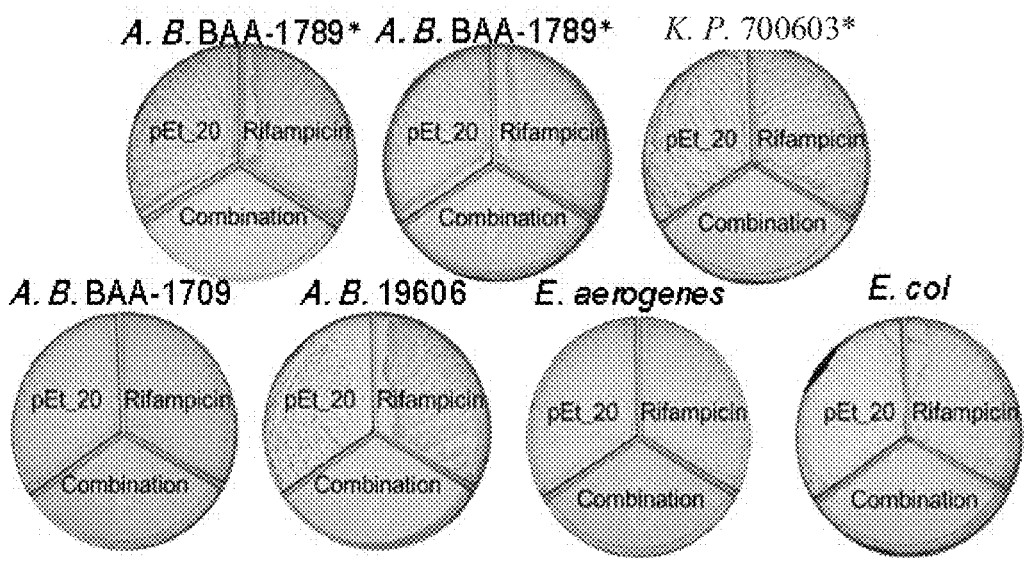

FIG. 13

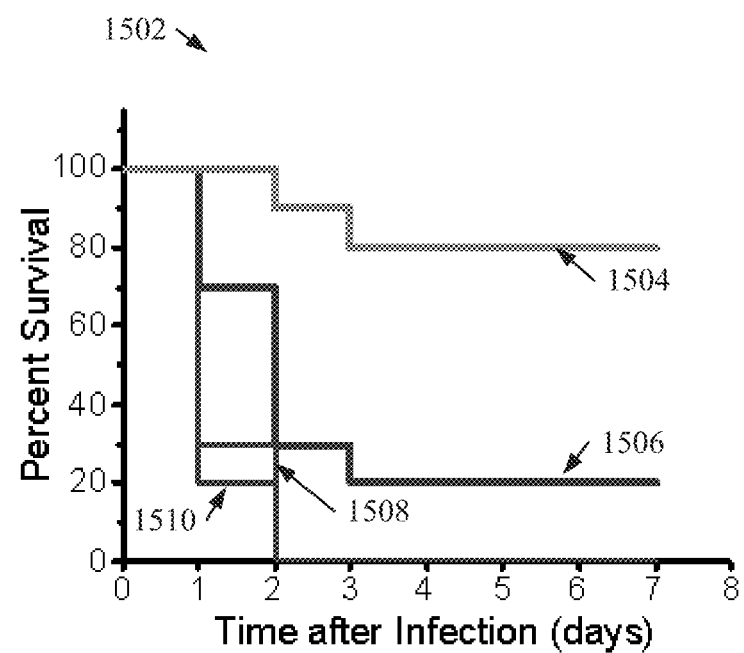
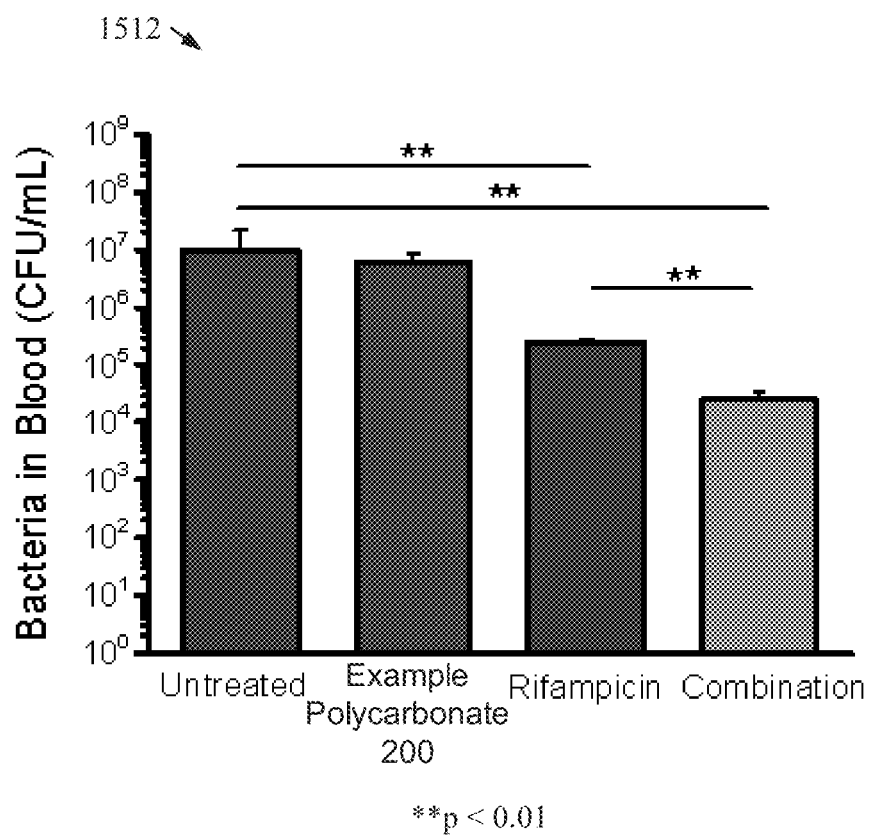
FIG. 15

1602 — ENHANCING AN ANTIMICROBIAL ACTIVITY OF AN ANTIBIOTIC BY A COMBINATION THERAPY, WHEREIN THE COMBINATION THERAPY CAN COMPRISE THE ANTIBIOTIC AND A POLYCARBONATE POLYMER FUNCTIONALIZED WITH A GUANIDINIUM FUNCTIONAL GROUP

1604 — INTERACTING THE POLYCARBONATE POLYMER WITH A CYTOSOLIC PROTEIN TARGETED BY THE ANTIBIOTIC

ENHANCING AN ANTIMICROBIAL ACTIVITY OF AN ANTIBIOTIC BY A COMBINATION THERAPY, WHEREIN THE COMBINATION THERAPY CAN COMPRISE THE ANTIBIOTIC AND A POLYIONENE POLYMER, AND WHEREIN THE POLYIONENE POLYMER COMPRISES A TEREPHTHALAMIDE STRUCTURE ⬅ 1702

⬇

GENERATING, BY THE POLYIONENE POLYMER, A HOLE IN A BIOLOGICAL MEMBRANE OF A MICROBE TARGETED BY THE ANTIBIOTIC ⬅ 1704

```
┌─────────────────────────────────────────────────────────────┐
│  REDUCING THE EFFECTIVE DOSAGE OF AN ANTIBIOTIC BY A         │ ← 1802
│  COMBINATION THERAPY, WHEREIN THE COMBINATION                │
│  THERAPY COMPRISES THE ANTIBIOTIC AND AN                     │
│  ANTIMICROBIAL POLYMER TO TREAT A MICROBIAL INFECTION        │
└─────────────────────────────────────────────────────────────┘
                              │
                              ▼
┌─────────────────────────────────────────────────────────────┐
│  GENERATING, BY THE ANTIMICROBIAL POLYMER, A HOLE IN A       │ ← 1804
│  BIOLOGICAL MEMBRANE OF A MICROBE TARGETED BY THE            │
│  ANTIBIOTIC, WHEREIN THE ANTIMICROBIAL POLYMER IS A          │
│  POLYIONENE POLYMER COMPRISING ONE OR MORE                   │
│  TEREPHTHALAMIDE STRUCTURES                                  │
└─────────────────────────────────────────────────────────────┘
```

INHIBITING A DEVELOPMENT OF A RESISTANCE TO AN ANTIBIOTIC BY A MICROBE USING A COMBINATION THERAPY, WHEREIN THE COMBINATION THERAPY COMPRISES THE ANTIBIOTIC AND AN ANTIMICROBIAL POLYMER ⤹ 1902

PRECIPITATING, BY THE ANTIMICROBIAL POLYMER, A CYTOSOLIC PROTEIN COMPRISED WITHIN THE MICROBE, WHEREIN THE ANTIMICROBIAL POLYMER IS A POLYCARBONATE POLYMER FUNCTIONALIZED WITH A GUANIDINIUM FUNCTIONAL GROUP ⤹ 1904

ADMINISTERING A COMBINATION THERAPY TO TREAT AN INFECTION OF A MICROBE, WHEREIN THE COMBINATION THERAPY COMPRISES AN ANTIBIOTIC AND AN ANTIMICROBIAL POLYMER, AND WHEREIN THE ANTIMICROBIAL POLYMER ENHANCES AN ANTIMICROBIAL ACTIVITY OF THE ANTIBIOTIC — 2002

GENERATING, BY THE ANTIMICROBIAL POLYMER, A HOLE IN A BIOLOGICAL MEMBRANE OF A MICROBE TARGETED BY THE ANTIBIOTIC, WHEREIN THE ANTIMICROBIAL POLYMER IS A POLYIONENE POLYMER COMPRISING ONE OR MORE TEREPHTHALAMIDE STRUCTURES — 2004

UTILIZING POLYMERS AND ANTIBIOTICS TO ENHANCE ANTIMICROBIAL ACTIVITY AND INHIBIT ANTIBIOTIC RESISTANCE

BACKGROUND

The subject disclosure relates to utilizing a mixture of polymers and antibiotics to enhance antimicrobial activity and/or inhibit antibiotic resistance, and more specifically, to utilizing one or more polymers to enhance the antimicrobial activity of one or more antibiotics and/or inhibit the antibiotic resistance of one or more microbes.

A surge of antibiotic resistance accompanied with a dearth of new antibiotics has made antibiotic-resistant microbial (e.g., bacterial) infection a significant medical challenge. To treat antibiotic-resistant infections, particularly caused by Gram-negative bacteria, the monotherapy of current antibiotics may no longer be adequate. Even for polymyxin antibiotics (e.g., polymyxin B and/or colistin), the conventional last-resort treatment for antibiotic-resistant Gram-negative bacterial infections, the resistance has recently been increasingly found in clinical isolates. As an alternative approach, a combination of different antibiotics or antibiotic with non-antibiotic adjuvant has attracted attention. For example, rifampicin has been used in combination with colistin to treat antibiotic-resistant *A. baumannii*, and the combination has shown synergistic effect in vitro and in vivo. The synergistic effect may reduce doses of colistin and rifampicin to mitigate their nephrotoxicity and hepatotoxicity, respectively. This combination was also reported recently to lower the mutant prevention concentration of colistin for *A. baumannii*, indicating that selective growth of colistin-resistant sub-population could be prevented. However, a randomized clinical trial showed no reduction of 30-day mortality of patient infected with extensively antibiotic-resistant *A. baumannii*.

Thus, antibiotic-resistant microbial infections are becoming increasingly abundant, thereby diminishing the effectiveness of traditional antibiotic treatments. As a result, combinations of conventional antibiotics with more toxic polymyxin antibiotics have been created in attempt to treat and/or inhibit the antibiotic-resistant microbial infections. However, these antibiotic combinations retain an undesirable level of toxicity to human patients.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, methods that can regard one or more combination therapies comprising polymers in conjunction with antibiotics are described.

According to an embodiment, a method is provided. The method can comprise enhancing an antimicrobial activity of an antibiotic by a combination therapy. The combination therapy can comprise the antibiotic and a polycarbonate polymer functionalized with a guanidinium functional group. An advantage of such a method can be increased effectiveness of the antibiotic towards antibiotic-resistant microbes. In some examples, the enhancing the antimicrobial activity of the antibiotic can comprise interacting the polycarbonate polymer with a cytosolic protein, enzyme, and/or gene targeted by the antibiotic. An advantage of such a method can be the achievement of a synergistic antimicrobial effect between the antibiotic and the polycarbonate polymer.

According to an embodiment, a method is provided. The method can comprise enhancing an antimicrobial activity of an antibiotic by a combination therapy. The combination therapy can comprise the antibiotic and a polyionene polymer. Further, the polyionene polymer can comprise a terephthalamide structure. An advantage of such a method can be the broadening of the antimicrobial spectrum applicable to treat an antibiotic-resistant bacterium. In some examples, the enhancing the antimicrobial activity of the antibiotic can comprises generating, by the polyionene polymer, a hole in a biological membrane of a microbe targeted by the antibiotic. An advantage of such a method can be increased permeability of the microbe's biological membrane.

According to an embodiment, a method is provided. The method can comprise reducing an effective dosage of an antibiotic by a combination therapy. The combination therapy can comprise the antibiotic and an antimicrobial polymer. An advantage of such a method can be a reduction in the effective dosage of a toxic antibiotic to treat antibiotic-resistant bacteria. In some examples, the antimicrobial polymer can be a polymer selected from a group consisting of a polycarbonate polymer functionalized with a guanidinium functional group and a polyionene polymer comprises a terephthalamide structure. An advantage of such a method can be that antibiotic resistance of a bacterium can be prevented and/or delayed by enhanced bacterial membrane permeability, which can be caused by the polyionene polymer, and/or by precipitating cytosolic proteins and/or genes targeted by the antibiotic, which can be caused by the polycarbonate polymer.

According to an embodiment, a method is provided. The method can comprise inhibiting a development of a resistance to an antibiotic by a microbe using a combination therapy. The combination therapy can comprise the antibiotic and an antimicrobial polymer. An advantage of such a method can include the use of antibiotics while minimizing a risk of the target bacteria developing a resistance to the antibiotics. In some examples, the antimicrobial polymer can be a polymer selected from a group consisting of a polycarbonate polymer functionalized with a guanidinium functional group and a polyionene polymer comprising a terephthalamide structure. An advantage of such a method can be the achievement of higher antimicrobial potency and lower toxicity, as compared to traditional combination therapies.

According to an embodiment, a method is provided. The method can comprise administering a combination therapy to treat an infection of a microbe. The combination therapy can comprise an antibiotic and an antimicrobial polymer. Also, the antimicrobial polymer can enhance an antimicrobial activity of the antibiotic. An advantage of such a method can be a reduced influence of one or more efflux pumps located within the microbe. In some examples, the antimicrobial polymer can be a polymer selected from a group consisting of a polycarbonate polymer functionalized with a guanidinium functional group and a polyionene polymer comprising a terephthalamide structure. An advantage of such a method can be that the antimicrobial polymer can increase membrane permeability of the microbe and/or by bind cytosolic proteins and/or genes of the microbe targeted by the antibiotic.

BRIEF DESCRIPTION OF THE DRAWINGS

FIG. 5 illustrates a diagram of an example, non-limiting table that can depict the efficacy of one or more combination therapies that can comprise one or more polymers in conjunction with one or more antibiotics in accordance with one or more embodiments described herein.

FIG. 7 illustrates a diagram of an example, non-limiting table that can depict the efficacy of one or more combination therapies that can comprise one or more polymers in conjunction with one or more antibiotics in accordance with one or more embodiments described herein.

FIG. 12 illustrates a diagram of an example, non-limiting table that can depict the efficacy of one or more combination therapies that can comprise one or more polymers in conjunction with one or more antibiotics in accordance with one or more embodiments described herein.

FIG. 13 illustrates a diagram of example, non-limiting tables and/or graphs that can depict the efficacy of one or more combination therapies that can comprise one or more polymers in conjunction with one or more antibiotics in accordance with one or more embodiments described herein.

FIG. 15 illustrates a diagram of example, non-limiting graphs that can depict the efficacy of one or more combination therapies that can comprise one or more polymers in conjunction with one or more antibiotics in accordance with one or more embodiments described herein.

FIG. 16 illustrates a flow diagram of an example, non-limiting method that can facilitate enhancing antimicrobial activity of one or more antibiotics via one or more combination therapies comprising a combination of polymers and/or antibiotics in accordance with one or more embodiments described herein.

FIG. 17 illustrates a flow diagram of an example, non-limiting method that can facilitate enhancing antimicrobial activity of one or more antibiotics via one or more combination therapies comprising a combination of polymers and/or antibiotics in accordance with one or more embodiments described herein.

FIG. 18 illustrates a flow diagram of an example, non-limiting method that can facilitate enhancing antimicrobial activity of one or more antibiotics via one or more combination therapies comprising a combination of polymers and/or antibiotics in accordance with one or more embodiments described herein.

FIG. 19 illustrates a flow diagram of an example, non-limiting method that can facilitate enhancing antimicrobial activity of one or more antibiotics via one or more combination therapies comprising a combination of polymers and/or antibiotics in accordance with one or more embodiments described herein.

FIG. 20 illustrates a flow diagram of an example, non-limiting method that can facilitate enhancing antimicrobial activity of one or more antibiotics via one or more combination therapies comprising a combination of polymers and/or antibiotics in accordance with one or more embodiments described herein.

DETAILED DESCRIPTION

Figure 1:
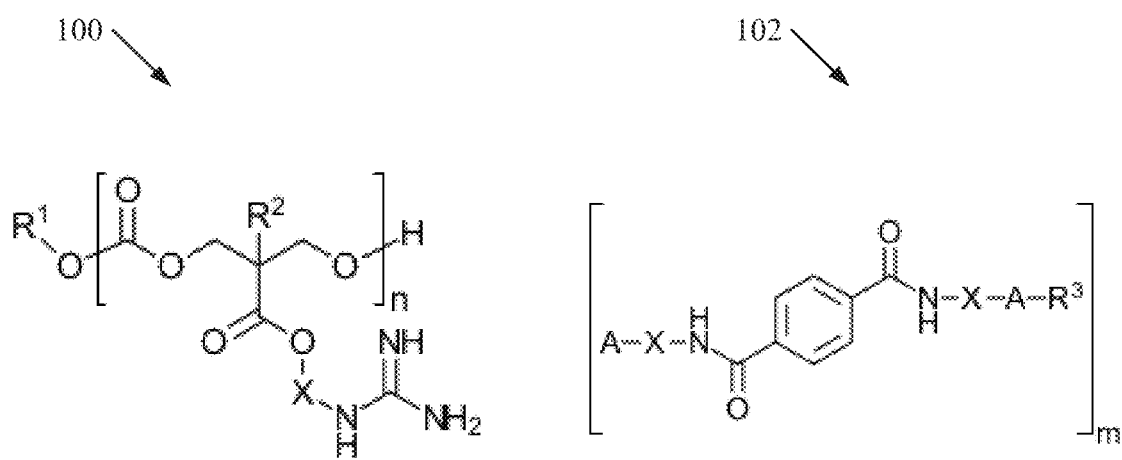
FIG. 1 illustrates a diagram of example, non-limiting chemical structures that can characterize various polymers that can be utilized with one or more antibiotics in one or more combination therapies in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Given the above problems with the conventional antibiotics and/or antibiotic combinations (e.g., ineffectiveness and/or toxicity), one or more embodiments described herein can be utilized to produce a solution to one or more of these problems in the form of a combination of one or more antibiotics and/or polymers. Methods implementing such a combination can have an advantage of enhancing antimicrobial activity while also inhibiting and/or delaying antibiotic resistance of one or more bacteria. For example, three potential benefits of the combination of one or more antibiotics and/or polymers can include, but are not limited to: broadening the effective antimicrobial spectrum by combining two or more antimicrobial agents with different targets;

creating a synergistic effect achieved between the one or more antibiotics and/or polymers (e.g., which can reduce non-specific toxicity of the subject combination therapy); and/or inhibiting (e.g., mitigating, negating, and/or delaying) resistance development of one or more bacteria by acting on various targets.

Various embodiments of the present invention can be directed to one or more methods regarding combination therapy that can utilize a combination of one or more polymers with one or more antibiotics to improve activity of the one or more antibiotics and/or inhibit (e.g., prevent, mitigate, and/or otherwise delay) antibiotic resistance of one or more bacteria. For example, in one or more embodiments the one or more polymers can comprise one or more guanidinium-functionalized polycarbonates and/or one or more cationic polyionenes. Further, the one or more polymers can have synergistic antimicrobial effect with the one or more antibiotics as the cellular uptake of the antibiotics can be enhanced with the increase of bacterial membrane permeability caused by the one or more polyionenes and/or due to binding of one or more target proteins and/or genes by one or more guanidinium-functionalized polycarbonates. Also, the combination of the one or more polymers and the one or more antibiotics can lower the effective dose of polymers and/or antibiotics, resulting in higher antimicrobial potency and lower toxicity. In addition, the antibiotic resistance of one or more bacteria can be inhibited (e.g., mitigated, prevented, and/or delayed) as the enhanced bacterial membrane permeability (e.g., attributed by the one or more polyionenes) can reduce the influence of efflux pump (e.g., which can be a resistance mechanism for a variety of antibiotics).

As used herein, the term "combination therapy" can refer to the use of multiple chemical compounds to treat an illness and/or disease. The chemical compounds can comprise pharmaceutical compounds such as antibiotics. Additionally, the chemical compounds can comprise compounds other than pharmaceutical compounds, such as antimicrobial polymers (e.g., functionalized polycarbonates and/or polyionenes). The multiple chemical compounds can be used in combination to achieve one or more synergistic effects, which can enhance and/or facilitate one or more therapeutic treats of the chemical compounds. In addition, the combination can comprise various types of chemical compounds. For example, one or more pharmaceutical compounds can be combined with one or more antimicrobial polymers in one or more combination therapies. Further, treating the illness can comprise: inhibiting the illness, eradicating the illness, delaying the illness, mitigating the illness, reducing the development of a resistance to treatment by the illness, a combination thereof, and/or the like. Moreover, the illness (e.g., an infection) can be caused by one or more microbes (e.g., bacteria, such as Gram-negative bacteria).

Unless otherwise stated, materials utilized to facilitate the experiments, tables, charts, diagrams, and/or the like described herein can be acquired from the following sources. The bacteria *Acinetobacter baumannii* ("*A. baumannii*") (e.g., strains BAA-1709,19606, BAA-1789 (antibiotic-resistant), and/or BAA-1792 (antibiotic-resistant)), *Staphylococcus aureus* ("*S. aureus*") (e.g., strain 6538), *Escherichia coli* ("*E. coli*") (e.g., strain 25922), *Pseudomonas aeruginosa* ("*P. aeruginosa*") (e.g., strain 9027), and/or *Klebsiella pneumoniae* (*K. pneumoniae*) (e.g., strain 700603) can be acquired from American Type Culture Collection ("ATCC"). The antibiotics rifampicin, tetracycline, azithromycin, ciprofloxacin, ceftazidime, and/or colistin can be acquired from Medchem Express. Benzylpenicillin ("penicillin g") can be acquired from Sigma-Aldrich. Gentamicin can be acquired from Gold Biotechnology. Polymyxin B can be acquired from MERCK®. Imipenem can be acquired from Merck Sharp & Dohme. (N-(3-triethylammoniumpropyl)-4-(6-(4-diethylamino)phenyl)hexatrienyl)pyridinium dibromide) ("MM 4-64 dye") can be acquired from Santa Cruz. SYTOX® green can be acquired from Life Technologies.

FIG. 1 illustrates a diagram on example, non-limiting chemical structures that can characterize one or more polymers that can be utilized in combination with one or more antibiotics in one or more combination therapies directed against one or more bacteria (e.g., one or more antibiotic-resistant bacteria) in accordance with one or more embodiments. Repetitive description of like elements employed in other embodiments described herein is omitted for sake of brevity. As shown in FIG. 1, one or more guanidium-functionalized polycarbonates and/or one or more cationic polyionenes can be utilized in combination with one or more antibiotics in accordance with one or more embodiments described herein.

The first chemical structure 100 shown in FIG. 1 can characterize one or more guanidium-functionalized polycarbonates that can be utilized in combination with one or more antibiotics in accordance with one or more embodiments described herein. As shown in FIG. 1, the first chemical structure 100 can comprise one or more functional groups. For instance, "$R^1$", as shown in FIG. 1, can represent a first functional group. The first functional group can comprise, for example, one or more alkyl groups and/or aryl groups. For example, the one or more first functional groups (e.g., represented by "$R^1$") can comprise, but are not limited to: carboxyl groups, carbonyl groups, ester groups, ether groups, ketone groups, amine groups, phosphine groups, urea croups, carbonate groups, alkenyl groups, hydroxyl groups, a combination thereof, and/or the like. Additionally, "$R^2$", as shown in FIG. 1, can represent a second functional group. The second functional group can comprise, for example, one or more alkyl groups and/or aryl groups. For example, the one or more second functional groups (e.g., represented by "$R^2$") can comprise, but are not limited to: carboxyl groups, carbonyl groups, ester groups, ether groups, ketone groups, amine groups, phosphine groups, urea croups, carbonate groups, alkenyl groups, hydroxyl groups, a combination thereof, and/or the like. Moreover, "X", as shown in FIG. 1, can represent one or more spacer structures. The one or more spacer structures can comprise, for example, one or more alkyl groups and/or aryl groups. For example, the one or more spacer structures (e.g., represented by "X") can comprise, but are not limited to: carboxyl groups, carbonyl groups, ester groups, ether groups, ketone groups, amine groups, phosphine groups, urea croups, carbonate groups, alkenyl groups, hydroxyl groups, a combination thereof, and/or the like. Lastly, "n", as shown in FIG. 1, can represent an integer greater than or equal to one. For example, "n" can represent an integer ranging from, for example, greater than or equal to one and less than or equal to 1000 (e.g., 20). As shown in FIG. 1, the one or more polycarbonates characterized by the first chemical structure 100 can be functionalized with one or more guanidinium groups (e.g., bonded to the one or more polycarbonates via the one or more spacer structures "X").

The second chemical structure 102 shown in FIG. 1 can characterize one or more cationic polyionenes. As used herein, the term "ionene" can refer to a polymer unit, a copolymer unit, and/or a monomer unit that can comprise a nitrogen cation and/or a phosphorus cation distributed along, and/or located within, a molecular backbone, thereby providing a positive charge. Example nitrogen cations include, but are not limited to: quaternary ammonium cations, protonated secondary amine cations, protonated tertiary amine cations, and/or imidazolium cations. Example, phosphorus cations include, but are not limited to: quaternary phosphonium cations, protonated secondary phosphine cations, and protonated tertiary phosphine cations. As used herein, the term "molecular backbone" can refer to a central chain of covalently bonded atoms that form the primary structure of a molecule. In various embodiments described herein, side chains can be formed by bonding one or more functional groups to a molecular backbone. As used herein, the term "polyionene" can refer to a polymer that can comprise a plurality of ionenes. For example, a polyionene can comprise a repeating ionene.

As shown in FIG. 1, the second chemical structure 102 can comprise a degradable molecular backbone. Further, the degradable molecular backbone can comprise one or more terephthalamide structures. In various embodiments, the cationic polyionenes characterized by the second chemical formula 102 can be derived from polyethylene terephthalate (PET), wherein the one or more terephthalamide structures can be derived from the PET. However, one or more embodiments of the second chemical formula 102 can comprise a terephthalamide structure derived from one or more molecules other than PET. The "A" in FIG. 1 can represent one or more cations. For example, "A" can represent one or more cations selected from a group that can include, but is not limited to: one or more nitrogen cations, one or more phosphorus cations, and/or a combination thereof. For instance, "A" can represent one or more nitrogen cations selected from a group that can include, but is not limited to: one or more protonated secondary amine cations, one or more protonated tertiary amine cations, one or more quaternary ammonium cations, one or more imidazolium cations, and/or a combination thereof. In another instance, "A" can represent one or more phosphorus cations selected from a group that can include, but is not limited to: one or more protonated secondary phosphine cations, one or more protonated tertiary phosphine cations, one or more quaternary phosphonium cations, and/or a combination thereof.

The one or more cations (e.g., represented by "A" in the second chemical structure 102) can be covalently bonded to one or more spacer structures (e.g., represented by "X") to form, at least a portion, of the degradable molecular backbone. The one or more spacer structures can link the one or more cations to the one or more terephthalamide structures, thereby comprising the molecular backbone. For example, the one or more spacer structures can have any desirable formation, including, but not limited to: chain formations, ring formations, and/or a combination thereof. For instance, "X" can represent one or more spacer structures that can comprise an alkyl chain having greater than or equal to two carbon atoms and less than or equal to 15 carbon atoms.

As shown in FIG. 1, in various embodiments, the second chemical structure 102 can comprise cations (e.g., represented by "A") at a plurality of locations along the molecular backbone. For example, cations can be located at either end of the molecular backbone (e.g., as illustrated in FIG. 1). However, in one or more embodiments of the second chemical structure 102, the molecular backbone can comprise less or more cations than the two illustrated in FIG. 1.

Further, "$R^3$", as shown in FIG. 1, can represent one or more hydrophobic functional groups in accordance with the various embodiments described herein. For example, the one or more hydrophobic functional groups can comprise one or more alkyl groups and/or one or more aryl groups. For instance, the hydrophobic functional group can be derived from a dialkyl halide. The one or more hydrophobic functional groups (e.g., represented by "$R^3$" in FIG. 1) can be covalently bonded to one or more of the cations (e.g., represented by "A" in FIG. 1) and/or the molecular backbone, which can comprise the one or more cations (e.g., represented by "A" in FIG. 1), one or more spacer structures (e.g., represented by "X" in FIG. 1), and/or one or more terephthalamide structures. In addition, the "m" shown in FIG. 1 can represent an integer greater than or equal to two and less than or equal to one thousand.

Figure 2:
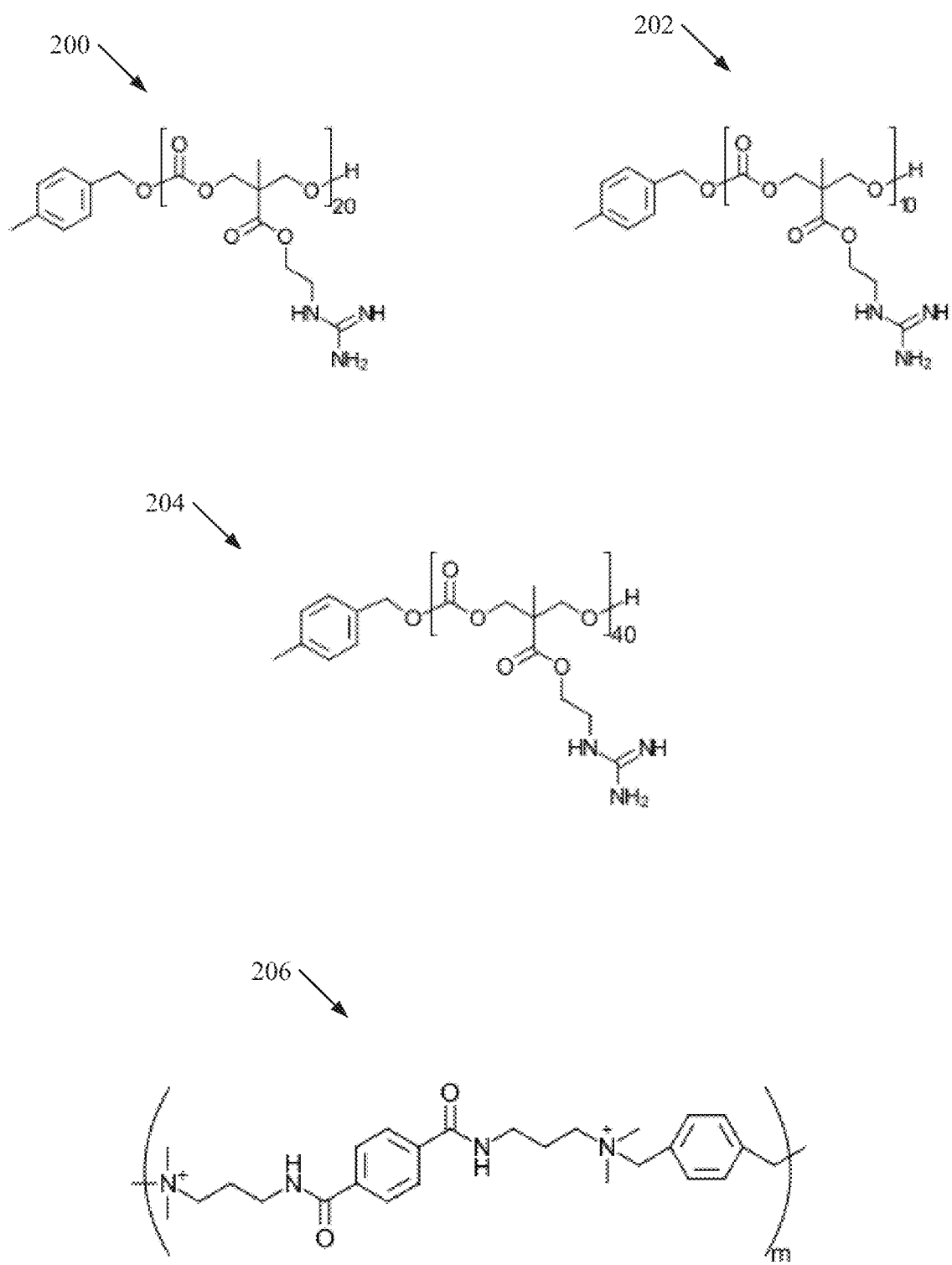
FIG. 2 illustrates a diagram of example, non-limiting polymers that can be utilized with one or more antibiotics in one or more combination therapies in accordance with one or more embodiments described herein.

FIG. 2 illustrates a diagram of example, non-limiting polymers that can be utilized in conjunction with one or more antibiotics to facilitate one or more combination therapies in accordance with one or more embodiments described herein. Repetitive description of like elements employed in other embodiments described herein is omitted for sake of brevity. For example, FIG. 2 depicts an example polycarbonate 200, a second example polycarbonate 202, a third example polycarbonate 204, and/or an example polyionene 206. The example polycarbonate 200 can be characterized by the first chemical structure 100, and/or the example polyionene 206 can be characterized by the second chemical structure 102. Also, as shown in FIG. 2, "m" shown can represent an integer greater than or equal to two and less than or equal to one thousand.

Figure 3:
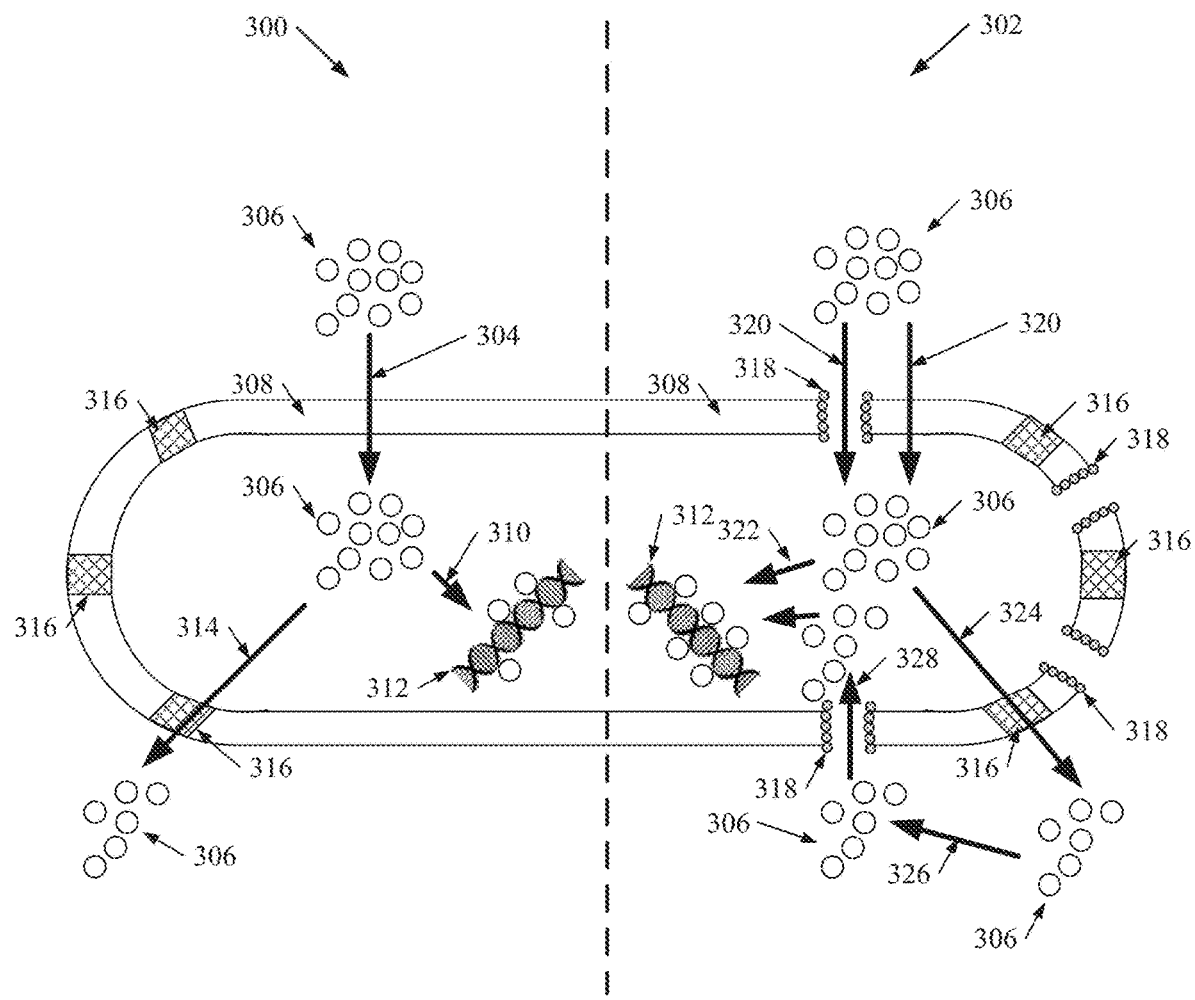
FIG. 3 illustrates a diagram of an example, non-limiting antimicrobial mechanism that can be facilitated by one or more combination therapies comprising one or more polymers in conjunction with one or more antibiotics in accordance with one or more embodiments described herein.

FIG. 3 illustrates a diagram of an example, non-limiting antimicrobial mechanism that can be implemented by one or more combination therapies, which can utilize one or more polymers characterized by the first chemical structure 100 and/or the second chemical structure 102 in conjunction with one or more antibiotics in accordance with one or more embodiments described herein. Repetitive description of like elements employed in other embodiments described herein is omitted for sake of brevity. As shown in FIG. 3, a dashed line in the middle of the drawings separates FIG. 3 into a left side and a right side. The left side can depict a first antimicrobial mechanism 300, while the right side can depict a second antimicrobial mechanism 302. Both the first antimicrobial mechanism 300 and/or the second antimicrobial mechanism 302 can be directed towards an exemplary bacterium. For example, the exemplary bacteria can be Gram-negative bacteria and/or Grain-positive bacteria.

The first antimicrobial mechanism 300 can characterize antimicrobial activity of one or more conventional antibiotic therapies and/or conventional combination therapies. For example, at a first stage 304 of the first antimicrobial mechanism 300, one or more antibiotics 306 (e.g., rifampicin, tetracycline, azithromycin, ciprofloxacin, ceftazidime, colistin, a combination thereof, and/or the like) can pass through a membrane 308 of the subject bacterium and enter an interior of the bacterium. For instance, the membrane 308 (e.g., comprising a lipid bilayer) can separate the interior of the subject bacterium from the environment surrounding the subject bacterium. At the second stage 310 of the first antimicrobial mechanism 300, a first portion of the one or more antibiotics 306 can remain in the interior of the bacterium and target one or more deoxyribonucleic acid ("DNA") segments 312. However, as shown by the third stage 314 of the first antimicrobial mechanism 300, a second portion of the one or more antibiotics 306 can be ejected from the bacterium by one or more efflux pumps 316 located in the membrane 308. Thus, the bacterium can use the one or more efflux pumps 316 to minimize the amount of antibiotics 306 that target the one or more DNA segments 312, and can thereby develop an increased resistance to the one or more antibiotics 306.

The second antimicrobial mechanism 302 can characterize antimicrobial activity of one or more combination therapies comprising one or more polyionenes 318 in conjunction with one or more antibiotics 306 in accordance with one or more embodiments described herein. The one or more polyionenes 318 can be characterized by the second chemical structure 102. As shown in FIG. 3, the one or more polyionenes 318 can generate one or more holes in the membrane 308. At a first stage 320 of the second antimicrobial mechanism 302, the one or more antibiotics 306 can pass through the one or more holes generated by the one or more polyionenes 318 and/or through the membrane 308 into the interior of the bacterium. At the second stage 322 of the second antimicrobial mechanism 302, a first portion of the one or more antibiotics 306 can remain in the interior of the bacterium and target one or more DNA segments 312. Similar to the first antimicrobial mechanism 300; at the third stage 324 of the second antimicrobial mechanism 302, a second portion of the one or more antibiotics 306 can be ejected from the bacterium by one or more efflux pumps 316 located within the membrane 308.

However, at the fourth stage 326 of the second antimicrobial mechanism 302 the one or more antibiotics 306 can move towards one or more of the holes generated by the one or more polyionenes 318. Further, at the fifth stage 328 of the second antimicrobial mechanism 302 the one or more antibiotic 306 can pass through one or more of the polymer-generated holes and re-enter the interior of the bacterium, Once re-entering the bacterium, the second portion of the one or more antibiotics 306 can further target the one or more DNA segments 312.

As compared to the first antimicrobial mechanism 300, the one or more polyionenes 318 of the second antimicrobial mechanism 302 can enhance the antimicrobial activity of the one or more antibiotics 306 and/or inhibit (e.g., mitigate and/or delay) resistance development of one or more bacteria towards the one or more antibiotics 306. For example, the one or more polymer generated holes in the membrane 308 of the bacteria can enhance uptake of the one or more antibiotics 306 by the bacteria, and thereby can lower the effective dose of the one or more antibiotics 306. The permeability change induced by the one or more polyionenes 318 can reduce the influence of the bacteria's efflux pump 316, thereby inhibiting (e.g., mitigating and/or delaying) resistance development.

With regards to the one or more guanidinium functionalized polycarbonates that can be characterized by the first chemical structure 100, antimicrobial activity of the one or more antibiotics 306 can be enhanced based on a membrane 308 translocation followed by precipitation of one or more cytosolic proteins and/or genes (e.g., located in the one or more DNA segments 312). For example, the one or more guanidinium functional groups can form one or more multidentate hydrogen-bonds with one or more phosphate groups in the bacterial membrane 308. The one or more multidentate hydrogen-bonds can neutralize a charge of the membrane 308, and thus can promote membrane 308 translocation. After entering the bacteria cells, the one or more polycarbonates can interact with one or more cytosolic proteins and/or genes of the bacteria, which can be targeted by the one or more antibiotics 306, and can thus precipitate the cytosolic materials. Therefore, the one or more polycarbonates, which can be characterized by the first chemical structure 100, can enhance the antimicrobial activity of the one or more antibiotics 306 by binding and/or precipitating one or more cytosolic proteins and/or genes of the target bacteria.

Figure 4:
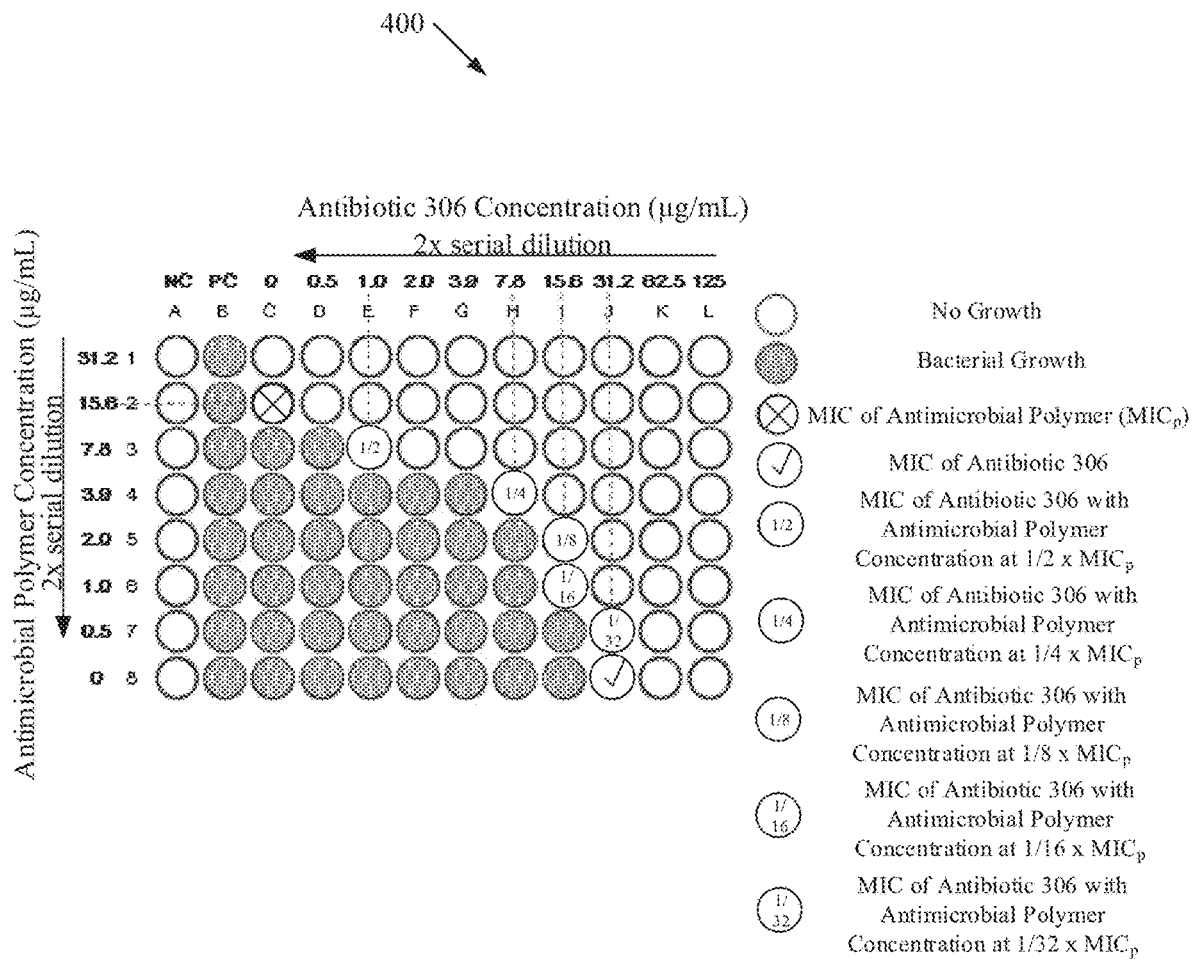
FIG. 4 illustrates a diagram of an example, non-limiting chart that can depict the efficacy of one or more combination therapies that can comprise one or more polymers in conjunction with one or more antibiotics in accordance with one or more embodiments described herein.

FIG. 4 illustrates a diagram of an example, non-limiting chart 400 that can depict the efficacy of one or more combination therapies, which can comprise one or more antimicrobial polymers (e.g., characterized by the first chemical structure 100 and/or the second chemical structure 102) in combination with one or more antibiotics 306 to facilitate the second antimicrobial mechanism 302 in accordance with one or more embodiments described herein. Repetitive description of like elements employed in other embodiments described herein is omitted for sake of brevity.

To evaluate antibacterial activity of antimicrobial polymer-antibiotic 306 combination therapies, the checkerboard method was used to create chart 400. By using this method, the minimum inhibitory concentration ("MIC") of antibiotics 306, antimicrobial polymers (e.g., characterized by the first chemical structure 100 and/or the second chemical structure 102), and/or antibiotics 306/antimicrobial polymers (e.g., characterized by the first chemical structure 100 and/or the second chemical structure 102) combination at varying polymer concentrations can be determined. MIC was measured based on the broth microdilution method. 50 microliters ("µL") of the example polycarbonate 200 at a serious of concentrations (micrograms per milliliter (µg/mL)) was added into a 96-well plate. Further, 50 µL, of antibiotics 306 (e.g., azithromycin, ciprofloxacin, ceftazidime, gentamicin, imipenem, penicillin G, rifampicin, and/or tetracycline) was added to the 96-well plate at different concentrations. Microbes (e.g., *S. aureus*, *A. baumannii*, *E. coli*, and/or *P. aeruginosa*) at exponential growth phases were diluted with 2-((3'-methyl-4'-hydroxyphenyl)azo)benzoic acid ("MHB") to about $10^5$ colony forming units ("CFU") per milliliter (CFU/mL), and 100 µL, of diluted microbes were added into each well of the 96-well plate with 100 µL of antimicrobial polymer-antibiotic 306 mixture. The 96-well plate was incubated at 37 degrees Celsius ("° C.") under shaking of 100 revolutions per minute ("rpm") for about 18 to 20 hours. The concentration at which there was no bacterial growth observed by naked eyes or a microplate reader at 600 nanometers (nm) was recorded as the MIC. The checkerboard experiments were performed three times for each antimicrobial polymer-antibiotic 306 combination.

FIG. 5 illustrates a diagram of an example, non-limiting table 500 that can further depict the efficacy one or more combination therapies, which can comprise one or more antimicrobial polymers (e.g., characterized by the first chemical structure 100 and/or the second chemical structure 102) in combination with one or more antibiotics 306 to facilitate the second antimicrobial mechanism 302 in accordance with one or more embodiments described herein. Repetitive description of like elements employed in other embodiments described herein is omitted for sake of brevity.

To compare the efficiency of an antimicrobial polymer/rifampicin combination and an antimicrobial polymer/polymyxin combination, the CFU of *A. baumannii* BAA-1709 under different combination treatments were studied. *A. baumannii* was incubated with rifampicin (e.g., at a concentration of 0.008 µg/mL) and the example polycarbonate 200, polymyxin B, and/or colistin at their final concentration of ½×MIC. After incubation at 37° C. with shaking at 100 rpm, the bacteria were collected at predetermined time points (e.g., 1, 2, 4, 8 and 24 hours) and then serially diluted. The diluted *A. baumannii* (e.g., 20 µL) was streaked onto LB agar plates and CFU was counted after an overnight incubation at 37° C. The results of CFU counting are presented as mean±standard deviation of triplicate samples.

To monitor development of antibiotic 306 resistance in *A. baumannii*, antibiotics 306 at sub-lethal doses were used in combination with the example polycarbonate 200 to repeatedly treat *A. baumannii* BAA-1709. With concentrations of the example polycarbonate 200 fixed at ¼ or ½×MIC, the MIC of antibiotics 306 was measured by the broth microdilution method. At half of the antibiotic 306 WC, the survived bacteria, which reached logarithmic growth phase, were collected for MIC measurement of the subsequent passage. The development of antibiotic 306 resistance was monitored for 30 passages and the MIC of the antibiotics 306 at ¼ or ½×MIC of the antimicrobial polymer (e.g., characterized by the first chemical structure 100 and/or the second chemical structure 102) was recorded for each passage. The resistance development of antibiotics 306 only and polymer only was also evaluated over 30 passages.

Synergistic effect between eight commonly used antibiotics 306 (e.g., azithromycin, ciprofloxacin, ceftazidime, gentamicin, imipenem, penicillin G, rifampicin, and/or tetracycline) and the example polycarbonate 200 against four bacteria (e.g., *A. baumannii*, *E. coli*, *P. aeruginosa*, and/or *S. aureus*) was evaluated by the checkerboard method. As shown in table 500, the MIC of azithromycin, imipenem, penicillin G and rifampicin against *A. baumannii* was significantly reduced as the concentration of antimicrobial polymer (e.g., characterized by the first chemical structure 100 and/or the second chemical structure 102) increased from $\frac{1}{16} \times MIC_p$ to $\frac{1}{2} \times MIC_p$, indicating that the antimicrobial polymer enhanced the potency of these antibiotics 306. In particular, the presence of example polycarbonate 200 can dramatically lower the MIC of rifampicin. For example, the MIC of rifampicin against *A. baumannii* was reduced to 0.13 μg/mL and 0.002 μg/mL in the presence of the antimicrobial polymer at $\frac{1}{4} \times MIC_p$, (e.g., 4 μg/mL) and $\frac{1}{2} \times MIC_p$ (e.g., 8 μg/mL), respectively. The MIC reduction can be over 2000 folds when it is compared with pure rifampicin. The significant enhancement in rifampicin potency was also observed for *E. coli*, with over 500-fold MIC reduction at $\frac{1}{2} \times MIC_p$ of the antimicrobial polymer. In addition to rifampicin, the presence of the example polycarbonate 200 can also enhance the potency of azithromycin against *E. coli* and tetracycline against *P. aeruginosa*. The MIC of antibiotics 306 against Gram-positive bacteria *S. aureus* showed no significant change with the addition of the antimicrobial polymer (e.g., characterized by the first chemical structure 100 and/or the second chemical structure 102), which is probably because the antibiotics 306 themselves are very effective and the cellular uptake of these antibiotics 306 by *S. aureus* is not an issue even without the antimicrobial polymer.

Similarly, example polyionene 206 showed synergistic effect with antibiotic 306 penicillin G, as presented in Table 1 below. For example, the MIC of penicillin G was reduced to 31.3 μg/mL at a polymer concentration of $\frac{1}{4} \times MIC_p$, and it was further reduced to 7.8 μg/mL when the polymer concentration was increased to $\frac{1}{2} \times MIC_p$

TABLE 1

| Antibiotic 306 | MIC of antibiotics 306 at different polymer concentration (μg/mL) | | | | |
|---|---|---|---|---|---|
| | w/o polymer | $\frac{1}{16} \times MIC_p$* | $\frac{1}{8} \times MIC_p$* | $\frac{1}{4} \times MIC_p$* | $\frac{1}{2} \times MIC_p$* |
| Penicillin G | 62.5 | 62.5 | 62.5 | 31.3 | 7.8 |

*MIC of example polyionene 206 (MIC$_p$) against *A. baumannii* (BAA-1709) is 7.8 μg/mL Polymyxins polymyxin B and/or colistin) have been reported to have strong synergy with rifampicin to treat *A. baumannii*. The efficacy of polymyxin B/rifampicin and colistin/rifampicin combinations was compared with that of an example polycarbonate 200/rifampicin combination. In the presence of polymyxin B or colistin at half of their MICs, the MIC of rifampicin was reduced to 0.5 μg/mL and 0.06 μg/mL, respectively, as presented in Table 2 below. However, the example polycarbonate 200 showed a greater synergistic effect with rifampicin. The MIC of rifampicin when combined with the antimicrobial polymer (e.g., characterized by the first chemical structure 100 and/or the second chemical structure 102) can be reduced to 0.002 μg/mL, which is over 30 folds and 250 folds lower than colistin/rifampicin and polymyxin B/rifampicin combinations, respectively. Moreover, the results also demonstrated a stronger synergistic effect between the polymer and rifampicin. Rifampicin at a low concentration of 0.008 μg/mL combined with example polycarbonate 200 can eradicate *A. baumannii* within one hour, while the mono-treatment with rifampicin or the combination treatment with polymyxin B/rifampicin or colistin/rifampicin showed no bactericidal activity over 24 h.

TABLE 2

| | MIC of rifampicin at different concentration of polymyxin B, colistin or example polycarbonate 200 (μg/mL) | | | |
|---|---|---|---|---|
| Adjuvants | w/o adjuvant | ⅛ × MIC* | ¼ × MIC* | ½ × MIC* |
| Polymyxin B | 3.9 | 3.9 | 2.0 | 0.5 |
| Colistin | 3.9 | 3.9 | 2.0 | 0.06 |
| Example Polycarbonate 200 | 3.9 | 2.0 | 0.13 | 0.002 |

*MIC of polymyxin B, colistin and example polycarbonate 200 against *A. baumannii*: 1.0 μg/mL, 1.0 μg/mL and 15.6 μg/mL.

Figure 6:
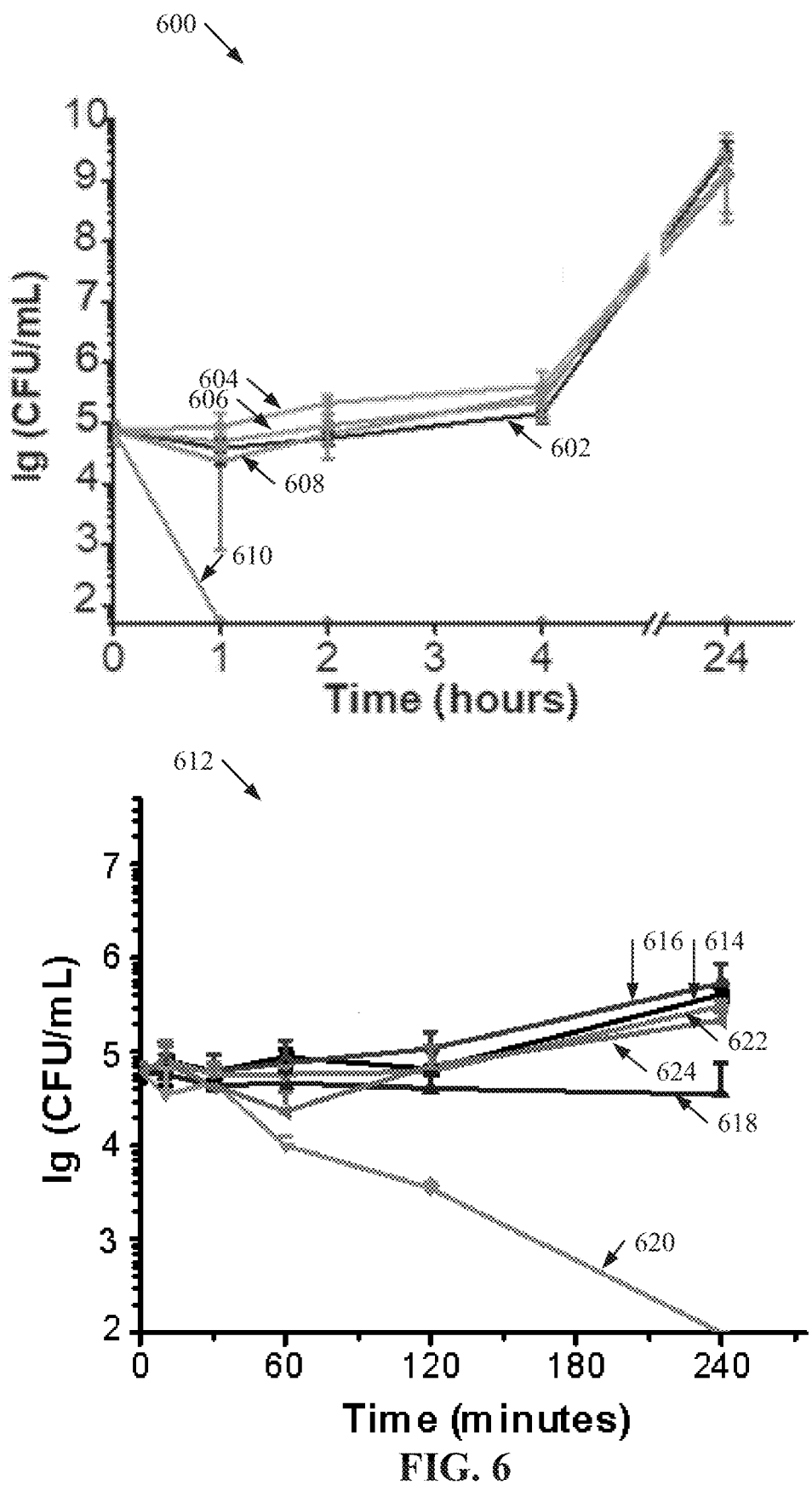
FIG. 6 illustrates a diagram of example, non-limiting graphs that can depict the efficacy of one or more combination therapies that can comprise one or more polymers in conjunction with one or more antibiotics in accordance with one or more embodiments described herein.

FIG. 6 illustrates a diagram of an example, non-limiting graph 600 that can depict the antimicrobial kinetics of rifampicin in various combination therapies against *A. baumannii*, such as a combination therapy comprising one or more antimicrobial polymers (e.g., characterized by the first chemical structure 100 and/or the second chemical structure 102) in accordance with the one or more embodiments described herein. Repetitive description of like elements employed in other embodiments described herein is omitted for sake of brevity.

As shown in FIG. 6, the first line 602 can represent a control group. The second line 604 can represent rifampicin at a concentration of 0.008 μg/mL. The third line 606 can represent a combination of rifampicin and polymyxin B. The fourth line 608 can represent a combination of rifampicin and colistin. Further, the fifth line 610 can represent a combination of rifampicin and example polycarbonate 200. Graph 600 can demonstrate that rifampicin at 0.008 μg/mL can eradicate *A. baumannii* within one hour only in the presence of the example polycarbonate 200 (e.g., at ½× MIC$_p$). The pure rifampicin or the rifampicin with polymyxin B or colistin at half their MICs displayed no bactericidal effect up to 24 hours.

Further, FIG. 6 illustrates a diagram of an example, non-limiting graph 612 that can depict the antimicrobial kinetic of various combination therapies comprising rifampicin, example polycarbonate 200, and/or colistin against rifampicin-resistant *A. baumannii* in accordance with one or more embodiments described herein. For example, FIG. 6 demonstrates that a combination of example polycarbonate 200 (e.g., at a concentration of 7.8 μg/mL) and rifampicin (e.g., at a concentration of 2.0 μg/mL) can eradicate rifampicin-resistant A. baumannii.

As shown in FIG. 6, the sixth line 614 can represent a control group. The seventh line 616 can represent a monotherapy comprising rifampicin. The eighth line 618 can represent a monotherapy comprising example polycarbonate 200. The ninth line 620 can represent a combination therapy comprising example polycarbonate 200 and rifampicin. The tenth line 622 can represent a monotherapy comprising colistin. Lastly, the eleventh line 624 can comprise a combination therapy comprising rifampicin and colistin. Graph 612 illustrates that the combination therapy of the antimicrobial polymer (e.g., example polycarbonate 200) and the antibiotic (e.g., rifampicin) can be the most effective inhibitor (e.g., eradicator) against antibiotic-resistant bacteria (e.g., rifampicin-resistant A. baumannii).

FIG. 7 illustrates a diagram of an example, non-limiting table 700 that can depict the efficacy of one or more combination therapies against various antibiotic-resistant strains of bacteria, wherein the one or more combination therapies can comprise a combination of one or more antibiotics 306 with one or more antimicrobial polymers (e.g., characterized by the first chemical structure 100 and/or the second chemical structure 102) in accordance with one or more embodiments described herein. Repetitive description of like elements employed in other embodiments described herein is omitted for sake of brevity.

In addition to antibiotic-susceptible bacteria, antibiotic-resistant strains of bacteria (e.g., indicated with a star in FIG. 7) were also employed to study the effect of antibiotic 306/example polycarbonate 200 combination on antibacterial activity. The antibacterial efficacy of the antimicrobial polymer (e.g., characterized by the first chemical structure 100 and/or the second chemical structure 102) against both susceptible and antibiotic-resistant strains of the bacteria can be similar with the same MIC value (e.g., 16 μg/mL). The antimicrobial polymer (e.g., characterized by the first chemical structure 100 and/or the second chemical structure 102) at sub-MIC concentrations can also exhibit a strong synergistic effect with rifampicin against antibiotic-resistant strains of bacteria (e.g., A. baumannii). For example, similar to susceptible strain ATCC 1709, the MIC of rifampicin can be reduced to 0.5 μg/mL at an antimicrobial polymer concentration of ¼×$MIC_p$, and can be further reduced to 0.002 μg/mL and 0.008 μg/mL at an antimicrobial polymer concentration of ½×$MIC_p$.

Figure 8:
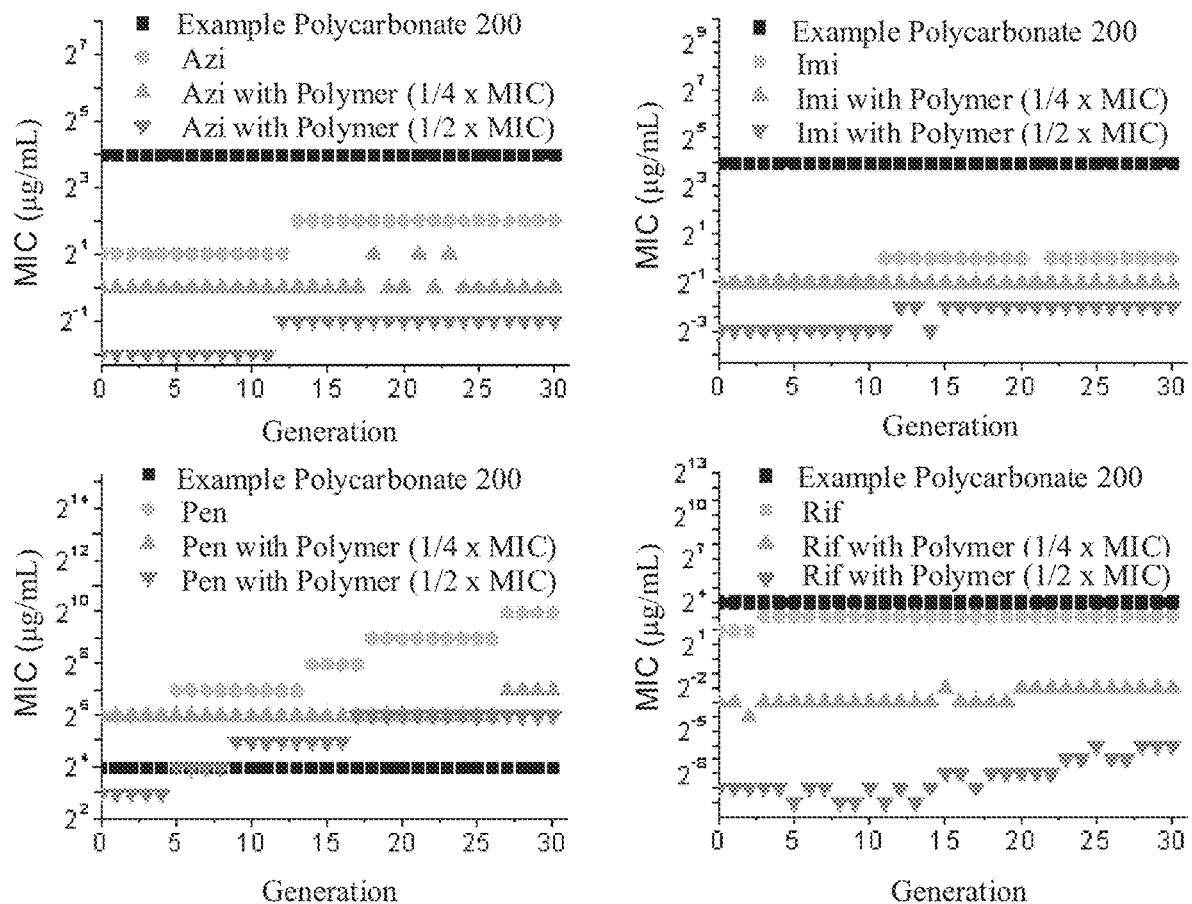
FIG. 8 illustrates a diagram of example, non-limiting graphs that can demonstrate the effectiveness of one or more combination therapies in inhibiting antibiotic-resistance in one or more bacteria (e.g., acinetobacter baumanni) in accordance with one or more embodiments described herein.

FIG. 8 illustrates a diagram of example, non-limiting graphs that can depict the antibiotic 306 resistance development profiles of a bacteria with regards to various combination therapies, including one or more combination therapies comprising a combination of one or more antibiotics 306 and/or one or more antimicrobial polymers (e.g., characterized by the first chemical structure 100 and/or the second chemical structure 102) in accordance with one or more embodiments described herein. Repetitive description of like elements employed in other embodiments described herein is omitted for sake of brevity.

As shown in FIG. 8, the MIC of the antibiotics 306 azithromycin ("Azi"), imipenem ("Imi"), penicillin ("Pen") and rifampicin ("Rif") with or without the example polycarbonate 200 ("polymer") were measured after exposing A. baumannii to each antibiotic 306 at sub-MIC continuously over 30 generations. The MIC of the example polycarbonate 200 at each generation was added as control. In the presence of the example polycarbonate 200 at ¼×$MIC_p$, the MIC of the antibiotics 306 did not increase or increased much slower than pure antibiotics 306 over 30 generations, and antibiotic resistance was effectively delayed. Although MICs of antibiotics 306 increased when the example polycarbonate 200 concentration of ½×$MIC_p$ was used, the MICs at generation 30 were still significantly lower than those of pure antibiotics 306.

In addition to the synergistic effect, the presence of the antimicrobial polymer (e.g., characterized by the first chemical structure 100 and/or the second chemical structure 102) can also delay the development of antibiotic resistance in bacteria (e.g., A. baumannii). For example, the antimicrobial polymers characterized by the first chemical structure 100 (e.g., example polycarbonate 200) and/or the second chemical structure 102 (e.g., example polyionene 206) can be less susceptible to resistance development by bacteria than common antibiotics 306. This was evidenced by the constant $MIC_p$ value over 30 generations. In contrast, the MIC for the antibiotics 306 azithromycin, imipenem, penicillin G and rifampicin all increased. Particularly, the rapid resistance evolution of A. baumannii against penicillin G was observed with MIC increased from 62.5 μg/mL to 125 μg/mL at generation 5 and 1000 μg/mL at generation 30. The presence of the antimicrobial polymer inhibited (e.g., delayed) antibiotic resistance development. For example, in the presence of the example polycarbonate 200 at ¼×$MIC_p$, the MIC of azithromycin and imipenem did not change over 30 generation, whereas resistance of the bacteria against penicillin G and rifampicin was delayed by 22 and 17 generations, respectively. Although antibiotic resistance occurred earlier when the antimicrobial polymer (e.g., characterized by the first chemical structure 100 and/or the second chemical structure 102) concentration of ½×$MIC_p$ was used, the MIC values of all antibiotics 306 were still lower than those in the presence of the example polycarbonate at ¼×$MIC_p$ due to the stronger synergistic effect at the higher antimicrobial polymer concentration.

Figure 9:
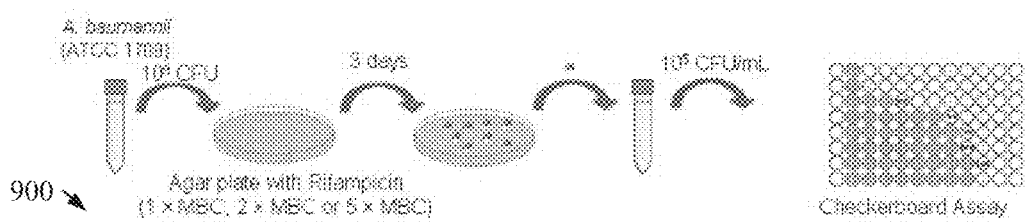
FIG. 9 illustrates a diagram of an example, non-limiting table that can depict the efficacy of one or more combination therapies that can comprise one or more polymers in conjunction with one or more antibiotics in accordance with one or more embodiments described herein.

FIG. 9 illustrates a diagram of an example, non-limiting table 900 that can demonstrate the efficacy and/or effectiveness of one or more combination therapies comprising one or more antimicrobial polymers (e.g., characterized by the first chemical structure 100 and/or the second chemical structure 102) in combination with one or more antibiotics 306 in accordance with one or more embodiments described herein. Repetitive description of like elements employed in other embodiments described herein is omitted for sake of brevity. For example, FIG. 9 demonstrates the efficacy and/or effectiveness of one or more combination therapies comprising rifampicin and example polycarbonate 200 against various strains and/or mutations of A. baumannii. Above table 900, FIG. 9 depicts the experimental conditions utilized to achieve the data presented in table 900. As shown in FIG. 9, the various embodiments described herein can be affective to enhance antimicrobial activity of one or more antibiotics 306 against both antibiotic-resistant bacteria and bacteria that is not antibiotic-resistant.

Figure 10:
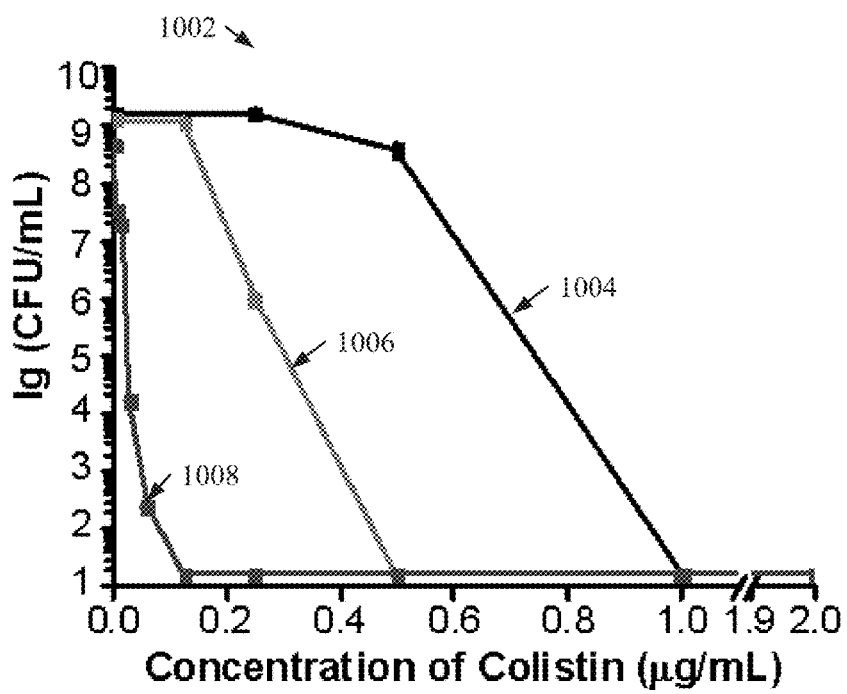
FIG. 10 illustrates a diagram of an example, non-limiting table and/or graph that can demonstrate the efficacy of one or more combination therapies in reducing the effective dose of an antibiotic (e.g., colistin) and an antimicrobial polymer with regards to various bacteria in accordance with one or more embodiments described herein.

FIG. 10 illustrates a diagram of an example, non-limiting table 1000 that can demonstrate the efficacy and/or effectiveness of one or more combination therapies comprising one or more antimicrobial polymers (e.g., characterized by the first chemical structure 100 and/or the second chemical structure 102) in combination with one or more antibiotics 306 in accordance with one or more embodiments described herein. Repetitive description of like elements employed in other embodiments described herein is omitted for sake of brevity. For example, table 1000 depicts the effects of one or more combination therapies comprising colistin in combination with example polycarbonate 200 against various bacteria (e.g., *E. coli, K. pneumoniae*, and/or *A. baumannii*). As shown in FIG. 10, even antibiotics (e.g., colistin) that have traditionally shown effectiveness against antibiotic-resistant bacteria can exhibit enhanced antimicrobial activity in the presence of one or more antimicrobial polymers.

Further, FIG. 10 illustrates a diagram of an example, non-limiting graph 1002 that can demonstrate that the effective dose of one or more toxic antibiotics 306 can be reduced by one or more combination therapies comprising one or more antimicrobial polymers (e.g., characterized by the first chemical structure 100 and/or the second chemical structure 102) in combination with the one or more toxic antibiotics. For example, graph 1002 shows that the effective dose of colistin against *A. baumannii* can be reduced as the concentration of antimicrobial polymer (e.g., example polycarbonate 200) increases. The results shown in graph 1002 were achieved after treatment for 18 hours. As shown in FIG. 10, the twelfth line 1004 can represent a monotherapy comprising colistin, the thirteenth line 1006 can represent a combination therapy comprising colistin and example polycarbonate 200 at 3.9 µg/mL (e.g., ¼×MIC), and/or the fourteenth line 1008 can represent a combination therapy comprising colistin and example polycarbonate 200 at 7.8 µg/mL (e.g., ½×MIC).

Figure 11:
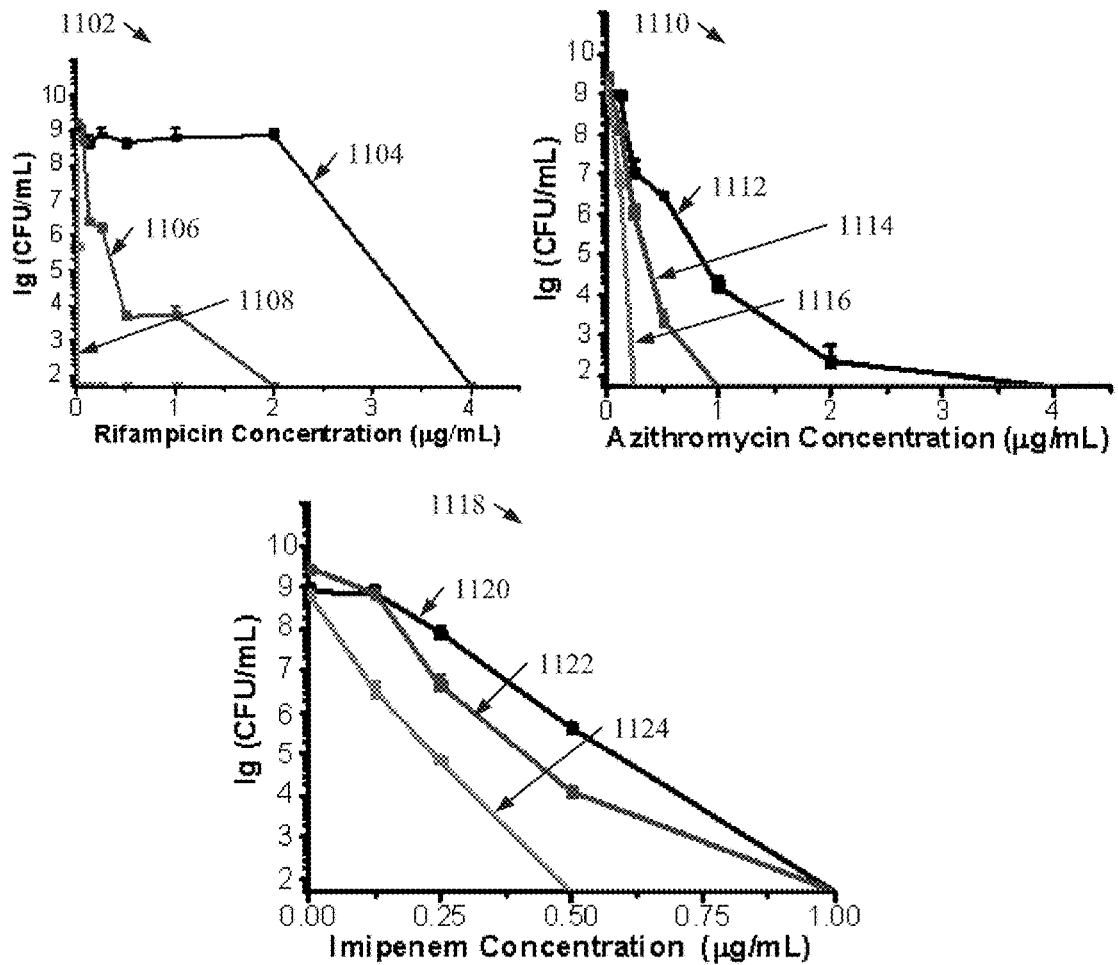
FIG. 11 illustrates a diagram of an example, non-limiting table and/or graph that can demonstrate the efficacy of one or more combination therapies in reducing the effective dose of one or more antibiotics with regards to various bacteria in accordance with one or more embodiments described herein.

FIG. 11 illustrates a diagram of an example, non-limiting table 1100 that can demonstrate the efficacy and/or effectiveness of one or more combination therapies comprising one or more antimicrobial polymers (e.g., characterized by the first chemical structure 100 and/or the second chemical structure 102) in combination with one or more antibiotics 306 in accordance with one or more embodiments described herein. Repetitive description of like elements employed in other embodiments described herein is omitted for sake of brevity. For example, table 1100 depicts the effects of three respective antibiotics 306 (e.g., rifampicin, azithromycin, and/or imipenem) combined with example polycarbonate 200 or colistin and challenged with *A. baumannii* (e.g., ATCC BAA-1709). As shown in FIG. 11, one or more combination therapies comprising one or more antimicrobial polymers (e.g., example polycarbonate 200) can achieve lower MICs of antibiotics 306 than combination therapies comprising colistin. Table 1100 shows that the MIC of antibiotics 306 can dramatically decrease when they are combined with one or more antimicrobial polymers (e.g., characterized by the first chemical structure 100 and/or the second chemical structure 102).

Further, FIG. 11 illustrates a diagram of example, non-limiting graph 1102, graph 1110, and/or graph 1118, which can depict that one or more combination therapies comprising one or more antimicrobial polymers (e.g., characterized by the first chemical structure 100, such as example polycarbonate 200, and/or the second chemical structure 102) and one or more antibiotics 306 can show stronger synergistic bactericidal effect than traditional combination therapies as evidenced by the bacterial count after 18 hours of treating *A. baumannii* (e.g., ATCC BAA-1709). For example, the one or more combination therapies comprising example polycarbonate 200 and a respective antibiotic 306 demonstrated stronger antimicrobial activity than monotherapies of the respective antibiotic 306 or other combination therapies of the respective antibiotic 306 in combination with colistin.

As shown in FIG. 11, graph 1102 can regard therapies comprising rifampicin as the respective antibiotic 306. Further, the fifteenth line 1104 can represent a monotherapy comprising rifampicin, the sixteenth line 1106 can represent a combination therapy comprising rifampicin and colistin at 0.5 µg/mL, and/or the seventeenth line 1108 can represent a combination therapy comprising rifampicin and example polycarbonate 200 at 7.8 µg/mL. Additionally, graph 1110 can regard therapies comprising azithromycin as the respective antibiotic 306. Further, the eighteenth line 1112 can represent a monotherapy comprising azithromycin, the nineteenth line 1114 can represent a combination therapy comprising azithromycin and colistin at 0.5 µg/mL, and/or the twentieth line 1116 can represent a combination therapy comprising azithromycin and example polycarbonate 200 at 7.8 µg/mL. Moreover, graph 1118 can regard therapies comprising imipenem as the respective antibiotic 306. The twenty-first line 1120 can represent a monotherapy comprising imipenem, the twenty-second line 1122 can represent a combination therapy comprising imipenem and colistin at 0.5 µg/mL, and/or the twenty-third line 1124 can represent a combination therapy comprising imipenem and example polycarbonate 200 at 7.8 µg/mL.

FIG. 12 illustrates a diagram of an example, non-limiting table 1200 that can demonstrate the efficacy and/or effectiveness of one or more combination therapies comprising one or more antimicrobial polymers (e.g., example polycarbonate 200) in combination with one or more antibiotics 306 (e.g., rifampicin, azithromycin, and/or imipenem) in accordance with one or more embodiments described herein. Repetitive description of like elements employed in other embodiments described herein is omitted for sake of brevity. As shown in FIG. 12, "A.B." can represent *A. baumannii*, "K.P." can represent *K. pneumoniae*, and the "*" can denote antibiotic-resistant strains of bacteria.

FIG. 13 illustrates a diagram of example, non-limiting table 1300 and/or table 1302, which can depict the synergistic effect of one or more combination therapies, which can comprise one or more antimicrobial polymers (e.g., characterized by the first chemical structure 100 and/or the second chemical structure 102) in combination with one or more antibiotics 306, against various bacteria (e.g., Gram-negative bacteria and/or Gram-positive bacteria) including antibiotic-resistant strains. Repetitive description of like elements employed in other embodiments described herein is omitted for sake of brevity. For example, the data presented in table 1300 and/or table 1302 can depict a strong synergistic effect with 128 to 2048 folds reduction of rifampicin MIC in the presence of the example polycarbonate 200 at a concentration of 7.8 µg/mL. With regards to table 1304, the concentration of example polycarbonate 200 is its ½ MIC (e.g., 7.8 µg/mL) for all the *A. baumannii* strains and *E. coli*, and 15.6 µg/mL for *E. aerogenes* and *K. pneumoniae*. Also, the concentration of rifampicin is its minimum bactericidal concentration ("MBC") (e.g., 0.015 µg/mL) for all the *A. baumannii* strains, 0.5 µg/mL for *E. coli* and *K. pneumoniae*, and 2 µg/mL for *E. aerogenes*.

Further, FIG. 13 illustrates a diagram of example, non-limiting photos 1304 of three-component plates with bacteria treated by example polycarbonate 200, rifampicin, and/or a combination thereof for 18 hours. As shown in FIG. 13, "pEt_20" can represent example polycarbonate 200. The photos 1304 can depict the enhanced bactericidal activity towards bacteria (e.g., Gram-negative bacteria and/or Gram-positive bacteria) exhibited by one or more combination therapies comprising one or more antimicrobial polymers in combination with one or more antibiotics 306. The data and/or photos 1304 depicted in FIG. 13 can be representative of three biological replicates, with the "*" denoting antibiotic-resistant strains of bacteria.

Figure 14:
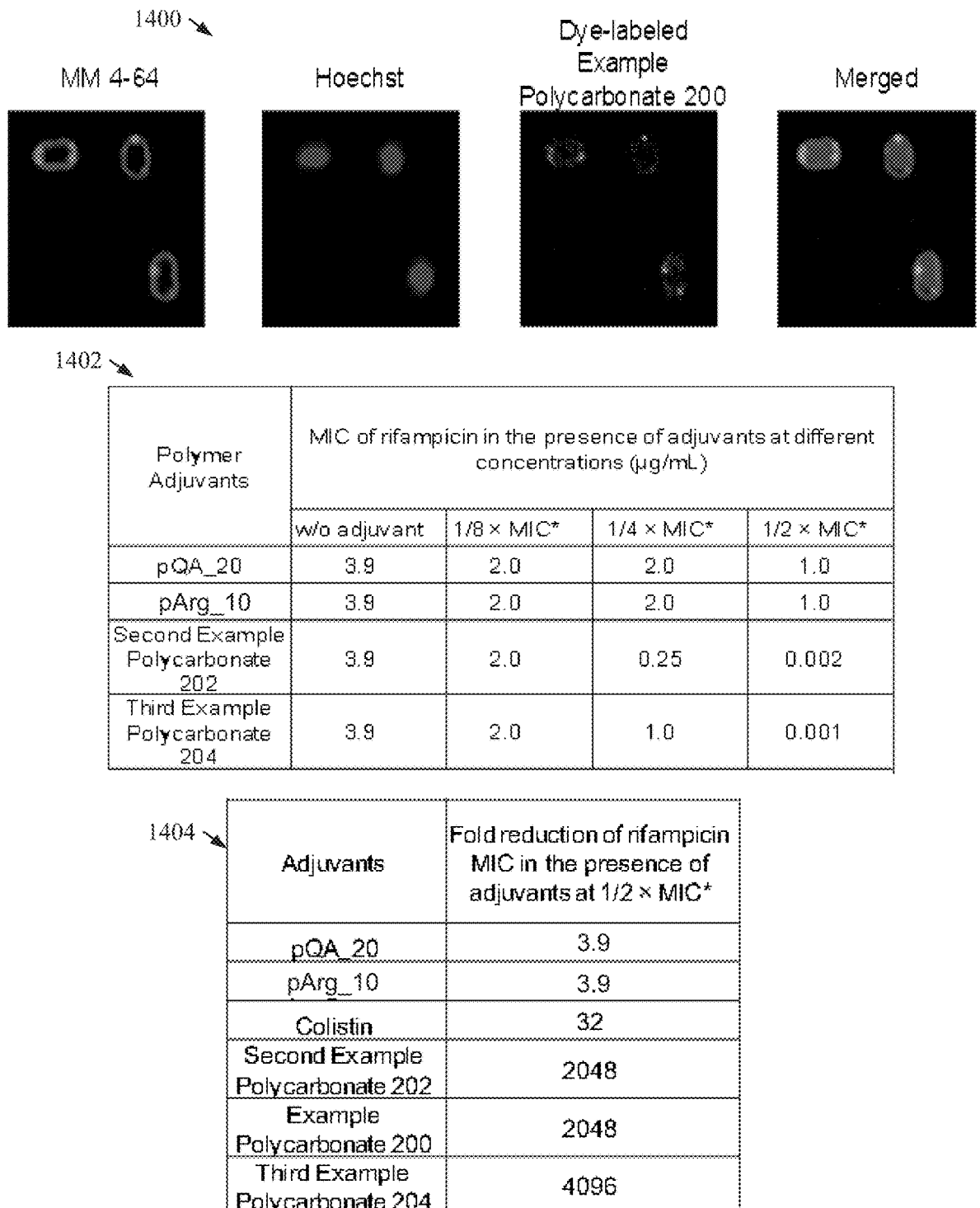
FIG. 14 illustrates a diagram of example, non-limiting tables that can depict the efficacy of one or more combination therapies that can comprise one or more polymers in conjunction with one or more antibiotics in accordance with one or more embodiments described herein.

FIG. 14 illustrates a diagram of example, non-limiting photos 1400 that can depict a mechanism of synergistic effect exhibited by one or more combination therapies comprising one or more antimicrobial polymers (e.g., characterized by the first chemical structure 100 and/or the second chemical structure 102) in combination with one or more antibiotics 306 in accordance with one or more embodiments described herein. Repetitive description of like elements employed in other embodiments described herein is omitted for sake of brevity. For example, the photos 1400 can depict Alexa Fluor 488 dye-labeled example polycarbonate 200 localized on the membrane 308 and/or cytoplasm of bacteria (e.g., *A. baumannii* "BAA-1709"). Further, FIG. 14 illustrates table 1402 and/or table 1404, which can depict the synergistic antimicrobial effect of one or more antibiotics 306 (e.g., rifampicin) combined with various antimicrobial polymers. As shown in FIG. 14, "pQA_20" can represent a quaternary ammonium-functionalized polycarbonate that can be characterized by the following chemical structure:

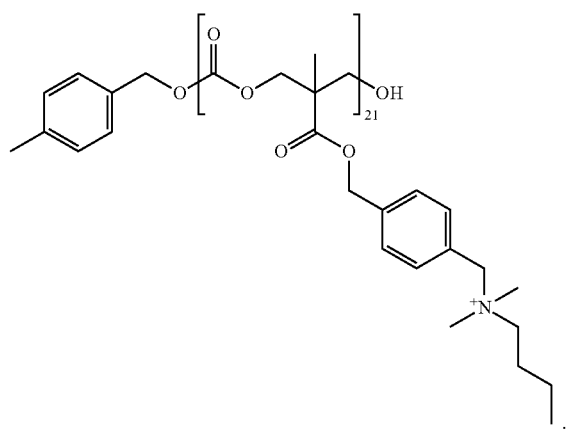

Additionally, "pArg_10" can represent an oligopeptide that can be characterized by the following chemical structure:

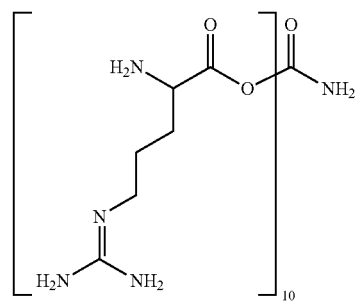

As demonstrated in table 1402 and/or table 1404, despite "pQA_20" and/or "pArg_10" comprising a nitrogen cation and/or a guanidinium functional group, the polymers did not achieve the same antimicrobial enhancements achieved by the antimicrobial polymers that can be characterized by the first chemical structure 100 and/or the second chemical structure 102.

FIG. 15 illustrates a diagram of example non-limiting graph 1502 and graph 1512 that can depict synergistic antimicrobial effects of one or more combination therapies, which can comprise one or more antimicrobial polymers (e.g., characterized by the first chemical structure 100 and/or the second chemical structure 102) in combination with one or more antibiotics 306, in a mouse bacteremia model in accordance with one or more embodiments described herein. Repetitive description of like elements employed in other embodiments described herein is omitted for sake of brevity. The mouse bacteremia model was created by injection of antibiotic-resistant *A. baumannii* (e.g., ATCC BAA-1789) at $1.3 \times 10^9$ CFU/mL (10 milliliters per kilogram (mL/kg)). Example polycarbonate 200 (e.g., 2 milligrams per kilogram (mg/kg)) and rifampicin (5 mg/kg) were sequentially injected into a tail vein of mice with two doses at 1 hour and 6 hours post infection. Survival of the mice was monitored from two weeks. Blood bacterial counts were obtained by taking blood from *A. baumannii* (e.g., $6.5 \times 10^8$ CFU/mL) infected mice at 24 hours post infection.

With regards to graph 1502, the twenty-fourth line 1504 can represent a combination therapy comprising example polycarbonate 200 and rifampicin. The twenty-fifth line 1506 can represent a monotherapy comprising rifampicin. The twenty-third line 1508 can represent a monotherapy comprising example polycarbonate 200. Also, the twenty-sixth line 1510 can represent no treatment. With regards to graph 1512, "p" can represent a probability value of the statistical model, wherein "p<0.01" can indicate significant difference between independent groups by a one-way Anova analysis.

As evidences by at least the drawings described herein (e.g., FIGS. 5-15), the combination of antimicrobial polymers (e.g., guanidinium-functionalized polycarbonates characterized by the first chemical structure 100 and/or polyionenes characterized by the second chemical structure 102) and antibiotics 306 can demonstrated a strong synergistic effect in antimicrobial (e.g., antibacterial) activity in the antibiotics 306 and/or prevention of antibiotic-resistance development in one or more bacteria. In the presence of the antimicrobial polymers, the potency of the antibiotics 306 (e.g., azithromycin, imipenem, penicillin G, rifampicin and/or tetracycline) against bacteria (e.g., Gram-negative bacteria and/or Gram-positive bacteria) can increase with at least 4-fold MIC reduction when the polymer concentration of $\frac{1}{2} \times MIC_p$ was used. Particularly, a greater synergistic effect between rifampicin and polycarbonates characterized by the first chemical structure 100 for both susceptible and antibiotic-resistant *A. baumannii* strains can be achieved with up to 2048-fold MIC reduction. The synergistic effect achieved by this combination is also higher than polymyxin B/rifampicin and colistin/rifampicin combinations with significantly reduced MIC and higher killing kinetics. In addition, the presence of the one or more antimicrobial polymers (e.g., characterized by the first chemical structure 100 and/or the second chemical structure 102) can slow down the development of antibiotic 306 resistance in bacteria. The antimicrobial polymers (e.g., characterized by the first chemical structure 100 and/or the second chemical structure 102) can enhance antimicrobial activity of antibiotics 306 against antibiotic-resistant microbes and delay antibiotic resistance development.

FIG. 16 illustrates a flow diagram of an example, non-limiting method 1600 that can facilitate treating (e.g., inhibiting, mitigating, eradicating, and/or delaying) one or more microbial infections with one or more combination therapies comprising one or more antibiotics 306 and one or more polycarbonate polymers in accordance with one or more embodiments described herein. Repetitive description of like elements employed in other embodiments described herein is omitted for sake of brevity.

At 1602, the method 1600 can comprise enhancing an antimicrobial activity of one or more antibiotics 306 (e.g., rifampicin, tetracycline, azithromycin, ciprofloxacin, ceftazidime, colistin, a combination thereof, and/or the like) using one or more combination therapies. The one or more combination therapies can comprise administering the one or more antibiotics 306 and one or more polycarbonate polymers functionalized with one or more guanidinium functional groups. The one or more polycarbonate polymers can be one or more antimicrobial polymers that can be characterized by the first chemical structure 100. The combination therapy can be administered, for example, to one or more patients suffering from one or more microbial infections (e.g., an infection of Gram-negative bacteria and/or Gram-positive bacteria such as *A. baumannii, Staphylococcus aureus, E. coli, P. aeruginosa, K. pneumoniae*, a combination thereof, and/or the like). Further, the one or more microbes comprising the infection can be antibiotic-resistant.

At 1604, the method 1600 can comprise interacting the one or more polycarbonate polymers with one or more cytosolic proteins, enzymes, and/or genes of a microbe targeted by the one or more antibiotics 306, The interacting at 1604 can enhance the antimicrobial activity of the one or more antibiotics 306.

FIG. 17 illustrates a flow diagram of an example, non-limiting method 1700 that can facilitate treating (e.g., inhibiting, mitigating, eradicating, and/or delaying) one or more microbial infections with one or more combination therapies comprising one or more antibiotics 306 and one or more polyionene polymers in accordance with one or more embodiments described herein. Repetitive description of like elements employed in other embodiments described herein is omitted for sake of brevity.

At 1702, the method 1700 can comprise enhancing an antimicrobial activity of one or more antibiotics 306 (e.g., rifampicin, tetracycline, azithromycin, ciprofloxacin, ceftazidime, colistin, a combination thereof, and/or the like) using one or more combination therapies. The one or more combination therapies can comprise administering the one or more antibiotics 306 and one or more polyionene polymers, which can comprise one or more terephthalamide structures. The one or more polyionene polymers can be one or more antimicrobial polymers (e.g., characterized by the first chemical structure 100 and/or the second chemical structure 102) that can be characterized by the second chemical structure 102. The combination therapy can be administered, for example, to one or more patients suffering from one or more microbial infections (e.g., an infection of Gram-negative bacteria and/or Gram-positive bacteria). Further, the one or more microbes comprising the infection can be antibiotic-resistant.

At 1704, the method 1700 can comprise generating, by the polyionene polymer, one or more holes in a biological membrane 308 of a microbe (e.g., *A. baumannii, Staphylococcus aureus, E. coli, P. aeruginosa, K. pneumoniae*, a combination thereof, and/or the like) targeted by the one or more antibiotics 306. The polymer-generated holes can increase the permeability of the membrane 308 to facilitate the enhancement of the antimicrobial activity at 1802.

FIG. 18 illustrates a flow diagram of an example, non-limiting method 1800 that can facilitate treating (e.g., inhibiting, mitigating, eradicating, and/or delaying) one or more microbial infections with one or more combination therapies comprising one or more antibiotics 306 and one or more antimicrobial polymers (e.g., characterized by the first chemical structure 100 and/or the second chemical structure 102) in accordance with one or more embodiments described herein. Repetitive description of like elements employed in other embodiments described herein is omitted for sake of brevity.

At 1802, the method 1800 can comprise reducing an effective dosage of one or more antibiotics 306 (e.g., rifampicin, tetracycline, azithromycin, ciprofloxacin, ceftazidime, colistin, a combination thereof, and/or the like) using a combination therapy. The combination therapy can comprise administering the one or more antibiotics 306 and one or more antimicrobial polymers to treat one or more microbial infections. The one or more antimicrobial polymers can be one or more polycarbonate polymers functionalized with one or more guanidinium functional groups (e.g., as characterized by the first chemical structure 100) and/or one or more polyionene 318 polymers comprising one or more terephthalamide structures (e.g., as characterized by the second chemical structure 102). Also, the one or more microbial infections can be infections of bacteria (e.g., Grain-negative bacteria and/or Grain-positive bacteria), which can further be antibiotic-resistant. In one or more embodiments, the one or more antibiotics 306 can be toxic; thus, the toxicity of the combination therapy can be reduced by the reduction in the effective dosage at 1802.

At 1804, the method 1800 can optionally comprise generating, by the one or more polyionene 318 polymers, one or more holes in a biological membrane 308 of a microbe (e.g., *A. baumannii, Staphylococcus aureus, E. coli, P. aeruginosa, K. pneumoniae*, a combination thereof, and/or the like) targeted by the one or more antibiotics 306. The polymer-generated holes can increase the permeability of the membrane 308 to facilitate the enhancement of the antimicrobial activity at 1802.

Additionally, wherein the one or more antimicrobial polymers are the one or more polycarbonates (e.g., characterized by the first chemical structure 100), the method 1800 can comprise binding and/or precipitating, by the one or more polycarbonate polymers, one or more cytosolic proteins and/or genes of a microbe targeted by the one or more antibiotics 306.

FIG. 19 illustrates a flow diagram of an example, non-limiting method 1900 that can facilitate treating (e.g., inhibiting, mitigating, eradicating, and/or delaying) one or more microbial infections with one or more combination therapies comprising one or more antibiotics 306 and one or more antimicrobial polymers (e.g., characterized by the first chemical structure 100 and/or the second chemical structure 102) in accordance with one or more embodiments described herein. Repetitive description of like elements employed in other embodiments described herein is omitted for sake of brevity.

At 1902, the method 1900 can comprise inhibiting a development of a resistance to one or more antibiotics 306 (e.g., rifampicin, tetracycline, azithromycin, ciprofloxacin, ceftazidime, colistin, a combination thereof, and/or the like) by one or more microbes using a combination therapy. The combination therapy can comprise administering the one or more antibiotics 306 and one or more antimicrobial polymers (e.g., to treat one or more microbial infections). The one or more antimicrobial polymers can be one or more polycarbonate polymers functionalized with one or more guanidinium functional groups (e.g., as characterized by the first chemical structure 100) and/or one or more polyionene 318 polymers comprising one or more terephthalamide structures (e.g., as characterized by the second chemical structure 102), Also, the one or more microbes can be a bacterium (e.g., Gram-negative bacteria and/or Gram-positive bacteria), which can further be antibiotic-resistant. In one or more embodiments, the inhibiting at 1902 can comprise negating and/or delaying the development of the microbe's antibiotic 306 resistance towards one or more subject antibiotics 306.

At 1904, the method 1900 can optionally comprise binding and/or precipitating, by the one or more polycarbonate polymers (e.g., characterized by the first chemical structure 100), one or more cytosolic proteins comprised within the microbe. Further, the one or more polycarbonates can bind and/or precipitate one or more genes of the microbe. The binding and/or precipitating at 1904 can facilitate the inhibiting at 1902.

Additionally, wherein the one or more antimicrobial polymers are the one or more polyionene 318 polymers, the method 1900 can comprise generating, by the one or more polyionene 318 polymers, one or more holes in a biological membrane 308 of a microbe (e.g., *A. baumannii, Staphylococcus aureus, E. coli, P. aeruginosa, K. pneumoniae*, a combination thereof, and/or the like) targeted by the one or more antibiotics 306. The polymer-generated holes can increase the permeability of the membrane 308 to enhance the microbe's cellular uptake of the one or more antibiotics 306 and thereby facilitate the inhibiting at 1902. Further, the polymer-generating holes can reduce the effectiveness of one or more efflux pumps 316 comprised within the microbe, which can thereby facilitate inhibiting the antibiotic 306 resistance development at 1902.

FIG. 20 illustrates a flow diagram of an example, non-limiting method 2000 that can facilitate treating (e.g., inhibiting, mitigating, eradicating, and/or delaying) one or more microbial infections with one or more combination therapies comprising one or more antibiotics 306 and one or more antimicrobial polymers (e.g., characterized by the first chemical structure 100 and/or the second chemical structure 102) in accordance with one or more embodiments described herein. Repetitive description of like elements employed in other embodiments described herein is omitted for sake of brevity.

At 2002, the method 2000 can comprise administering one or more combination therapies to treat one or more infections of one or more microbes. The one or more combination therapies can comprise one or more antibiotics 306 (e.g., rifampicin, tetracycline, azithromycin, ciprofloxacin, ceftazidime, colistin, a combination thereof, and/or the like) and one or more antimicrobial polymers. The one or more antimicrobial polymers can enhance an antimicrobial activity of the one or more antibiotics 306. Further, the one or more antimicrobial polymers can be one or more polycarbonate polymers functionalized with one or more guanidinium functional groups (e.g., as characterized by the first chemical structure 100) and/or one or more polyionene 318 polymers comprising one or more terephthalamide structures (e.g., as characterized by the second chemical structure 102). Also, the one or more microbes can be a bacterium (e.g., Gram-negative bacteria and/or Gram-positive bacteria), which can further be antibiotic-resistant. In one or more embodiments, the administering at 2102 can comprise administering the one or more antibiotics 306 and/or the one or more antimicrobial polymers to a patient simultaneously and/or sequentially.

At 2004, the method 2000 can optionally comprise generating, by the one or more polyionene 318 polymers, one or more holes in a biological membrane 308 of a microbe (e.g., *A. baumannii, Staphylococcus aureus, E. coli, P. aeruginosa, K. pneumoniae*, a combination thereof, and/or the like) targeted by the one or more antibiotics 306. The polymer-generated holes can facilitate the enhancement of antimicrobial activity at 2002 by enhancing the microbe's cellular uptake of the one or more antibiotics 306 (e.g., also inhibiting the development of antibiotic 306 resistance by the one or more microbes).

Additionally, wherein the one or more antimicrobial polymers are the one or more polycarbonates (e.g., characterized by the first chemical structure 100), the method 2000 can comprise binding and/or precipitating, by the one or more polycarbonate polymers, one or more cytosolic proteins and/or genes of the microbe targeted by the one or more antibiotics 306.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for treating a bacteria infection, comprising:
    contacting the bacteria infection with a combination therapy comprising an antibiotic and a polycarbonate polymer, wherein the polycarbonate polymer enhances an antimicrobial activity of the antibiotic, and wherein the polycarbonate polymer is characterized by a chemical structure:

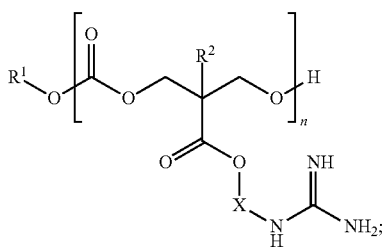

wherein "R¹" corresponds to a first functional group selected from a first group consisting of a first alkyl group and a first aryl group;

wherein "R²" corresponds to a second functional group selected from a second group consisting of a second alkyl group and a second aryl group;

wherein "X" corresponds to a spacer structure selected from a third group consisting of a third alkyl group and a third aryl group; and wherein "n" corresponds to an integer greater than or equal to 1 and less than or equal to one thousand.

2. The method of claim 1, wherein the enhancing the antimicrobial activity of the antibiotic comprises interacting the polycarbonate polymer with a cytosolic member targeted by the antibiotic, wherein the cytosolic member is selected from a group consisting of a protein, an enzyme, and a gene.

3. The method of claim 1, wherein the chemical structure is:

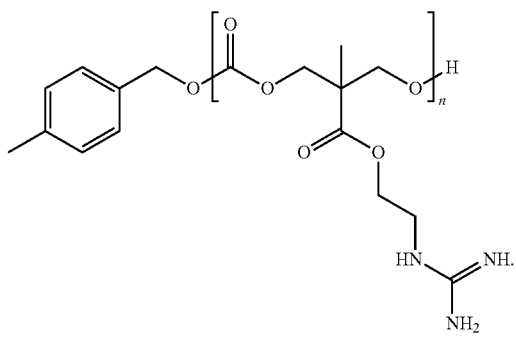

4. A method for reducing a minimum inhibitory concentration of an antibiotic selected from the group consisting of rifampicin, tetracycline, azithromycin, ciprofloxacin, ceftazidime, penicillin, gentamicin, and imipenem, comprising:

administering the antibiotic by a combination therapy comprising the antibiotic and a polycarbonate polymer, wherein the polycarbonate polymer enhances an antimicrobial activity of the antibiotic against a bacterium selected from the group consisting of *Acinetobacter baumannii, Staphylococcus aureus, Escherichia coli, Pseudomonas aeruginosa*, and *Klebsiella pneumoniae*, and wherein the polycarbonate polymer is characterized by a chemical structure:

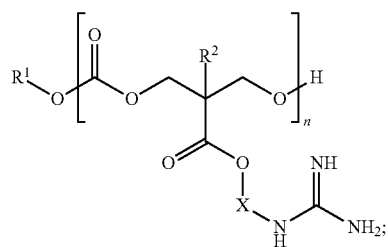

wherein "R¹" corresponds to a first functional group selected from a first group consisting of a first alkyl group and a first aryl group;

wherein "R²" corresponds to a second functional group selected from a second group consisting of a second alkyl group and a second aryl group;

wherein "X" corresponds to a spacer structure selected from a third group consisting of a third alkyl group and a third aryl group; and wherein "n" corresponds to an integer greater than or equal to 1 and less than or equal to one thousand.

5. The method of claim 4, wherein the antibiotic is toxic.

6. The method of claim 4, wherein the enhancing the antimicrobial activity comprises precipitating, by the polycarbonate polymer, a cytosolic member comprised within the bacterium, and wherein the cytosolic member is selected from a group consisting of a protein, an enzyme, and a gene.

7. A method for inhibiting a development of a resistance to an antibiotic by a bacterium, wherein the antibiotic is selected from the group consisting of rifampicin, tetracycline, azithromycin, ciprofloxacin, ceftazidime, penicillin, gentamicin, and imipenem, and wherein the bacterium is selected from the group consisting of *Acinetobacter baumannii, Staphylococcus aureus, Escherichia coli, Pseudomonas aeruginosa*, and *Klebsiella pneumoniae*, the method comprising:

administering a mixture of the antibiotic and a polycarbonate polymer to the bacterium, wherein the polycarbonate polymer enhances an antimicrobial activity of the antibiotic, and wherein the polycarbonate polymer is characterized by a chemical structure:

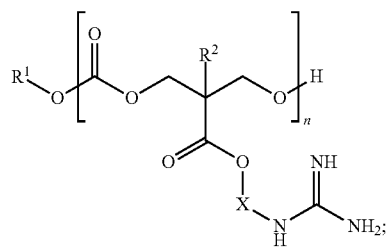

wherein "R¹" corresponds to a first functional group selected from a first group consisting of a first alkyl group and a first aryl group;

wherein "R²" corresponds to a second functional group selected from a second group consisting of a second alkyl group and a second aryl group;

wherein "X" corresponds to a spacer structure selected from a third group consisting of a third alkyl group and a third aryl group; and wherein "n" corresponds to an integer greater or equal to 1 and less than or equal to one thousand.

8. The method of claim 7, wherein the inhibiting comprises delaying the development of the resistance.

* * * * *